United States Patent
Ridaura et al.

(10) Patent No.: US 10,774,377 B1
(45) Date of Patent: Sep. 15, 2020

(54) USE OF UNIQUE MOLECULAR IDENTIFIERS FOR IMPROVED SEQUENCING OF TAXONOMICALLY RELEVANT GENES

(71) Applicant: Verily Life Sciences LLC, Mountain View, CA (US)

(72) Inventors: Vanessa Ridaura, San Francisco, CA (US); Jerrod George Schwartz, San Francisco, CA (US)

(73) Assignee: VERILY LIFE SCIENCES LLC, Mountain View, CA (US)

(*) Notice: Subject to any disclaimer, the term of this patent is extended or adjusted under 35 U.S.C. 154(b) by 205 days.

(21) Appl. No.: 15/726,254

(22) Filed: Oct. 5, 2017

(51) Int. Cl.
| | |
|---|---|
| C12Q 1/68 | (2018.01) |
| C12Q 1/686 | (2018.01) |
| C12N 9/12 | (2006.01) |

(52) U.S. Cl.
CPC ............ *C12Q 1/686* (2013.01); *C12N 9/1241* (2013.01)

(58) Field of Classification Search
None
See application file for complete search history.

(56) References Cited

U.S. PATENT DOCUMENTS

| | | | |
|---|---|---|---|
| 2012/0003657 A1* | 1/2012 | Myllykangas ....... | C12Q 1/6869 435/6.12 |
| 2014/0249037 A1 | 9/2014 | Fry et al. | |
| 2015/0132754 A1 | 5/2015 | Wang et al. | |

FOREIGN PATENT DOCUMENTS

| | | |
|---|---|---|
| EP | 2889380 A1 | 1/2015 |
| WO | 2016/095789 A1 | 6/2016 |

OTHER PUBLICATIONS

Wen et al. (PLoS One, 2017, 12(4):e0176716) (Year: 2017).*
Fu, G.K., et al., "Counting Individual DNA Molecules by the Stochastic Attachment of Diverse Labels," PNAS 108(22):9026-9031, May 2011.
Haas, B.J. et al., "Chimeric 16S rRNA sequence formation and detection in Sanger and 454-pyrosequenced PCR Amplicons," Genome Research 21(3):494-504, Mar. 2011, downloaded from <genome.cshlp.org> [retrieved Jun. 21, 2017].
Hug, H., and R. Schuler, "Measurement of the Number of Molecules of a Single mRNA Species in a Complex mRNA Preparation," J Theor Biol.221(4):615-24, Apr. 2003 (Author's Manuscript, 21 pages).
Islam, S. et al., "Quantitative Single-Cell RNA-seq With Unique Molecular Identifiers," Brief Communications in Nature Methods 11(2), Feb. 2014 [published online Dec. 22, 2013], 6 pages.
Kivioja, T. et al., "Counting Absolute Numbers of Molecules Using Unique Molecular Identifiers," Brief Communications in Nature Methods 9(1), Jan. 2012 [published online Nov. 20, 2011], 5 pages.
Hiatt, J.B., et al., "Single Molecule Molecular Inversion Probes for Targeted, High-Accuracy Detection of Low-Frequency Variation," Genome Research 23(5):843-854, May 2013.
Caporaso, J.G., et al., "Global Patterns of 16S rRNA Diversity at a Depth of Millions of Sequences Per Sample," PNAS 108(1):4516-4522, Mar. 2011.
Gohl, D.M., "Systematic Improvement of Amplicon Marker Gene Methods for Increased Accuracy in Microbiome Studies," Analysis in Nature Biotechnology, published online Jul. 25, 2016, 31 pages.
Faith, J.J., et al., "The Long-Term Stability of the Human Gut Microbiota," Science 341:1237439-1 to 1237439-8, Jul. 2013, downloaded from <www.sciencemag.org> [retrieved Jul. 10, 2013].
Schwartz, J.J., et al., "Accurate Gene Synthesis With Tag-Directed Retrieval of Sequence-Verified DNA Molecules," Brief Communications in Nature Methods 9(9), Sep. 2012 [published online Aug. 12, 2012], 5 pages.
Tremblay, J. et al., "Primer and Platform Effects on 16S rRNA Tag Sequencing," Frontiers in Microbiology, vol. 6, Aug. 4, 2015, 15 pages.
Zhang, T. et al., "454 Pyrosequencing Reveals Bacterial Diversity of Activated Sludge From 14 Sewage Treatment Plants," The ISME Journal (2012) 6, pp. 1137-1147 [published online Dec. 15, 2011], Jun. 2012.

* cited by examiner

*Primary Examiner* — Stephanie K Mummert
(74) *Attorney, Agent, or Firm* — Christensen O'Connor Johnson Kindness PLLC

(57) ABSTRACT

This disclosure generally relates to improved methods, compositions, and systems for detecting, quantifying, and characterizing genomic sequences from heterogeneous genomic samples. The disclosed methods include providing a unique molecular identifier to the initial target sequences prior to amplification and addition of indexing barcodes. The methods, compositions, and systems can be employed to accurately detect and quantify operational taxonomic units from heterogeneous samples and further to detect sequencing errors, e.g., chimeric sequences, which may occur during the development and sequencing of the library.

17 Claims, 11 Drawing Sheets
Specification includes a Sequence Listing.

SEQUENCE LISTING

```
<160> NUMBER OF SEQ ID NOS: 31

<210> SEQ ID NO 1
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
```

```
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t

<400> SEQUENCE: 1
nnnantnnng nnn                                                        13

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
gtgccagcmg ccgcggtaa                                                  19

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ggactachvg ggtwtctaat                                                 20

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gtgycagcmg ccgcggtaa                                                  19

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a, c, g, or t

<400> SEQUENCE: 5
ggactacnvg ggtwtctaat                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (12)..(12)
<223> OTHER INFORMATION: n is a, c, g, or t

<400> SEQUENCE: 6
agagtttgat cntggctcag                                                20

<210> SEQ ID NO 7
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 7
gtnttacngc ggckgctg                                                  18

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
agagtttgat cctggctcag                                                20

<210> SEQ ID NO 9
<211> LENGTH: 17
<212> TYPE: DNA
<213> ORGANISM: Artificial Sequence
<220> FEATURE:
<223> OTHER INFORMATION: Synthetic

<400> SEQUENCE: 9
attaccgcgg ctgctgg                                                   17

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
aaactyaaak gaattgacgg                                                20

<210> SEQ ID NO 11
<211> LENGTH: 15
<212> TYPE: DNA
<213> ORGANISM: Artificial Sequence
<220> FEATURE:
<223> OTHER INFORMATION: Synthetic

<400> SEQUENCE: 11
acgggcggtg tgtrc                                                     15

<210> SEQ ID NO 12
<211> LENGTH: 20
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t

<400> SEQUENCE: 12
agagtttgat cntggctcag                                                        20

<210> SEQ ID NO 13
<211> LENGTH: 20
<212> TYPE: DNA
<213> ORGANISM: Artificial Sequence
<220> FEATURE:
<223> OTHER INFORMATION: Synthetic'

<400> SEQUENCE: 13
ggactachvg ggtwtctaat                                                        20

<210> SEQ ID NO 14
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t

<400> SEQUENCE: 14
agagtttgat cntggctcag                                                        20

<210> SEQ ID NO 15
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n is a, c, g, or t

<400> SEQUENCE: 15
ggactacnvg ggtwtctaat                                                        20

<210> SEQ ID NO 16
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t

<400> SEQUENCE: 16
cctacgggng gcwgcag                                                           17

<210> SEQ ID NO 17
<211> LENGTH: 21
<212> TYPE: DNA
<213> ORGANISM: Artificial Sequence
<220> FEATURE:
<223> OTHER INFORMATION: Synthetic
```

<400> SEQUENCE: 17
gactachvgg gtatctaatc c                                              21

<210> SEQ ID NO 18
<211> LENGTH: 17
<212> TYPE: DNA
<213> ORGANISM: Artificial Sequence
<220> FEATURE:
<223> OTHER INFORMATION: Synthetic

<400> SEQUENCE: 18
cctacgggag gcagcag                                                   17

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
ccgtcaattc mtttragt                                                  18

<210> SEQ ID NO 20
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t

<400> SEQUENCE: 20
agagtttgat cntggctcag                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
cggttacctt gttacgactt                                                20

<210> SEQ ID NO 22
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(47)
<223> OTHER INFORMATION: n is a, c, g, or t

<400> SEQUENCE: 22
tcgtcggcag cgtcagatgt gtataagaga cagnnnnnnn nnnnnnngtg ccagcmgccg    60
cggtaa                                                               66

<210> SEQ ID NO 23
<211> LENGTH: 64
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(45)
<223> OTHER INFORMATION: n is a, c, g, or t

<400> SEQUENCE: 23
tcgtcggcag cgtcagatgt gtataagaga cagnnnnnnn nnnnngtgcc agcmgccgcg    60
gtaa                                                                64

<210> SEQ ID NO 24
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(43)
<223> OTHER INFORMATION: n is a, c, g, or t

<400> SEQUENCE: 24
tcgtcggcag cgtcagatgt gtataagaga cagnnnnnnn nnngtgccag cmgccgcggt    60
aa                                                                  62

<210> SEQ ID NO 25
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(43)
<223> OTHER INFORMATION: n is a, c, g, or t

<400> SEQUENCE: 25
tcgtcggcag cgtcagatgt gtataagaga cagnnnnnnn nnngtgccag cmgccgcggt    60
aa                                                                  62

<210> SEQ ID NO 26
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(49)
<223> OTHER INFORMATION: n is a, c, g, or t

<400> SEQUENCE: 26
gtctcgtggg ctcggagatg tgtataagag acaggnnnnn nnnnnnnnng gactachvgg    60 gtwtctaat                                                           69

<210> SEQ ID NO 27
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(47)
<223> OTHER INFORMATION: n is a, c, g, or t
```

<400> SEQUENCE: 27
gtctcgtggg ctcggagatg tgtataagag acaggnnnnn nnnnnnngga ctachvggt      60 wtctaat                                                                67

<210> SEQ ID NO 28
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(45)
<223> OTHER INFORMATION: n is a, c, g, or t

<400> SEQUENCE: 28
gtctcgtggg ctcggagatg tgtataagag acaggnnnnn nnnnggact achvgggtwt      60 ctaat                                                                 65

<210> SEQ ID NO 29
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(45)
<223> OTHER INFORMATION: n is a, c, g, or t

<400> SEQUENCE: 29
gtctcgtggg ctcggagatg tgtataagag acaggnnnnn nnnnggact achvgggtwt      60 ctaat                                                                 65

<210> SEQ ID NO 30
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(49)
<223> OTHER INFORMATION: n is a, c, g, or t

<400> SEQUENCE: 30
gtctcgtggg ctcggagatg tgtataagag acaggnnnnn nnnnnnnna gagtttgatc      60 mtggctcag                                                             69

<210> SEQ ID NO 31
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (36)..(49)
<223> OTHER INFORMATION: n is a, c, g, or t

<400> SEQUENCE: 31
gtctcgtggg ctcggagatg tgtataagag acaggnnnnn nnnnnnnna ttaccgcggc      60 tgctgg                                                                66

USE OF UNIQUE MOLECULAR IDENTIFIERS FOR IMPROVED SEQUENCING OF TAXONOMICALLY RELEVANT GENES

FIELD OF THE DISCLOSURE

The present disclosure generally relates to detecting and characterizing genomic sequences, such as in genomic sequencing and metagenomics analysis. More specifically, the disclosure provides improved approaches for developing sequencing libraries that provide for increased efficiency and sensitivity for accurately profiling the relative presence of genomic variants (e.g., genes representing operational taxonomic units) and avoiding bias imposed by errors in sequencing or library construction.

STATEMENT REGARDING SEQUENCE LISTING

The sequence listing associated with this application is provided in text format in lieu of a paper copy and is hereby incorporated by reference into the specification. The name of the text file containing the sequence listing is 61219_ST25.txt. The text file is 9 KB; was created on Oct. 4, 2017; and is being submitted via EFS-Web with the filing of the specification.

BACKGROUND

Diverse communities of microorganisms inhabit a wide range of environmental and biological niches and can have profound effects on their environments or hosts. For example, the human microbiota refers to the collection of eukaryotes, archaea, and bacterial species that live in close association with human epithelial surfaces such as the gut, the skin, and the nasal or oral cavities. The structure and the function of the bacterial and archeal components of microbiota communities have been associated with different aspects of host health and disease, including obesity, type-2 diabetes and a variety of cancer types. Considering the profound impact of the microbiota on many aspects of human health, it is of great interest to be able to profile and study the members of the microbiota community and assess their relative representation therein.

Initial methods attempting to culture the individuals from the microbiota (or from environmental niches) have provided only incomplete glimpses into the diverse communities because of the inability to culture many or most of the members. Furthermore, culturing does not provide an accurate quantification of relative abundance of any particular member. More recently, metagenomic sequencing has provided a much more comprehensive view of microbial communities and their structures because the approach does not rely on the ability to culture any particular organism. These analyses rely on the detection of sequence variation in select genetic markers to ascertain the presence and relative quantity of distinct taxa within a microbial community. An exemplary prokaryotic marker useful for such metagenomics analysis is the 16S rRNA gene. The 16S rRNA gene is composed of nine hypervariable regions (V1-V9), which allow researchers to differentiate between different bacterial and archeal species present in a given sample. Such analyses are dependent on amplification of the target genetic sequences by the Polymerase Chain Reaction (PCR) to provide sufficient template copies for sequencing. Accordingly, this approach has been shown to greatly overestimate the number and types of certain species present in a microbial community (e.g., a host-associated microbiota) due in part to amplification bias and PCR duplication and chimera generation. Conversely, the presence of rare species or species that are less conducive to target amplification can be obscured by the overrepresented or erroneous reads, thus resulting in an inaccurate profile of the subject community.

Modifications of target (e.g., 16S rRNA gene) PCR amplification have been proposed to more accurately quantitate the abundance of different bacterial and archeal taxa. For example, Low Error Amplicon Sequencing (LEA-Seq) has been described as a technique that is based on redundant sequencing of a set of linear PCR templates. However, this technique prioritizes quality over quantity of reads, by limiting the throughput of the reaction (i.e. fewer samples pooled per sequencing run) and relying on more expensive sequencing platforms (i.e. HiSeq®).

Accordingly, despite the advances in the art a need remains for improved methods of detecting and quantifying distinct microorganisms in a sample that are accurate, reproducible, and facile. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a method for generating a sequencing library. The method comprises contacting a sample comprising nucleic acids obtained from the heterogeneous microbial population with a first tagging polynucleotide primer, wherein the first tagging polynucleotide primer comprising a unique molecular identifier (UMI) sequence domain disposed between a first linker sequence and a sequence at the 3'-end that specifically anneals to, or anneals near to, a taxonomically relevant genomic sequence in the microbial population. The method further comprises providing conditions to allow the first tagging polynucleotide primer to specifically anneal to a target nucleic acid in the sample at or near to the taxonomically relevant genomic sequence. The method further comprises amplifying the taxonomically relevant genomic sequence to provide a plurality of amplicons comprising the first tagging polynucleotide primer sequence and the taxonomically relevant genomic sequence.

The method of this aspect can also comprise detecting operational taxonomic units (OTUs) in a heterogeneous microbial population. In this regard, the method further comprises in at least a portion of the plurality of amplicons, sequencing a segment of the amplicons comprising the first tagging polynucleotide primer sequence and the taxonomically relevant genomic sequence.

In another aspect, the disclosure provides a method of detecting a nucleic acid chimera formed during the generation of a sequencing library. The method comprises contacting a sample comprising nucleic acids from a heterogeneous microbial population with a first tagging polynucleotide and a second tagging polynucleotide that specifically anneal to either side of a taxonomically relevant genomic sequence in the microbial population, wherein the first tagging polynucleotide and the second tagging polynucleotide comprise a first unique molecular identifier (UMI) sequence domain and a second unique molecular identifier (UMI) sequence domain, respectively. The method further comprises amplifying the taxonomically relevant genomic sequence in a first stage to provide a first plurality of amplicons each comprising a first UMI sequence, a taxonomically relevant genomic sequence, and a second UMI sequence. The method further comprises contacting the first plurality of amplicons with a first indexing primer and a second indexing primer. The first indexing primer anneals to a first linker annealing sequence incorporated by the first tagging polynucleotide, and comprises a first index sequence domain and a first universal primer annealing sequence. The second indexing primer anneals to a second linker annealing sequence incorporated by the second tagging polynucleotide, and comprises a second index sequence domain and a second universal primer annealing sequence. The method further comprises amplifying the taxonomically relevant genomic sequence in a second stage to provide a second plurality of amplicons that each comprise the first universal primer annealing sequence, the first index sequence, a first UMI sequence, the taxonomically relevant genomic sequence, a second UMI sequence, the second index sequence, and the second universal primer annealing sequence. The method further comprises in at least a portion of the plurality of the second amplicons, sequencing the amplicons with universal primers that anneal to the first and second universal primer annealing sequences. A chimera is detected when the sequences of the first and/or second UMI sequence domain are discordant with other UMI domain pairs for that molecule.

In another aspect, the disclosure provides a method of detecting a nucleic acid chimera formed during the generation of a sequencing library. The method comprises contacting a sample comprising nucleic acids from heterogeneous microbial population with a first tagging polynucleotide and a second tagging polynucleotide. The first tagging polynucleotide comprises a first target annealing sequence at an end domain, a first linker sequence, and a first unique molecular identifier (UMI) sequence domain disposed between the first target annealing sequence and the first linker annealing sequence. The second tagging polynucleotide comprises a second target annealing sequence at an end domain, a second linker sequence, and a second unique molecular identifier (UMI) sequence domain disposed between the second target annealing sequence and the second linker sequence. The first and second target annealing sequences specifically anneal to either side of a taxonomically relevant genomic sequence in the microbial population. The method further comprises amplifying the taxonomically relevant genomic sequence in a first stage to provide a first plurality of amplicons each comprising a first UMI sequence, a taxonomically relevant genomic sequence, and a second UMI sequence. The method further comprises contacting the first plurality of amplicons with a first indexing primer and a second indexing primer. The first indexing primer is a forward primer that comprises a first linker annealing sequence at the 3'-end that anneals to the first linker sequence, a first universal primer annealing sequence, and a first index sequence domain disposed between the first linker sequence and the first universal primer annealing sequence. The second indexing primer is a reverse primer that comprises a second annealing linker sequence at the 3'-end that anneals to the second linker sequence, a second universal primer annealing sequence, and a second index sequence domain disposed between the second linker sequence and the second universal primer annealing sequence. The method further comprises further amplifying the taxonomically relevant genomic sequence in a second stage to provide a second plurality of amplicons that comprise the first universal primer annealing sequence, first index sequence, a first UMI sequence, the taxonomically relevant genomic sequence, a second UMI sequence, the second index sequence, and the second universal primer annealing sequence. The method further comprises in at least a portion of the plurality of the second amplicons, sequencing the amplicons with universal primers that anneal to the first and second universal primer annealing sequences. A chimera is detected when the sequences of the first and/or second UMI sequence domain are discordant with other UMI domain pairs for that molecule.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1A illustrates a method of a single UMI, two-stage dual index amplification strategy of hypervariable region V4 of the 16S rRNA gene. In the illustrated embodiment, the two index adapters are added in separate stages after the UMI is added. FIG. 1B illustrates a method of a dual UMI, single-stage dual index amplification strategy of hypervariable region V4 of the 16S rRNA gene. In the illustrated embodiment, the two index adapters are added in a single stage after a first and second UMI are added in a single initial step.

DETAILED DESCRIPTION

Figure 1A:
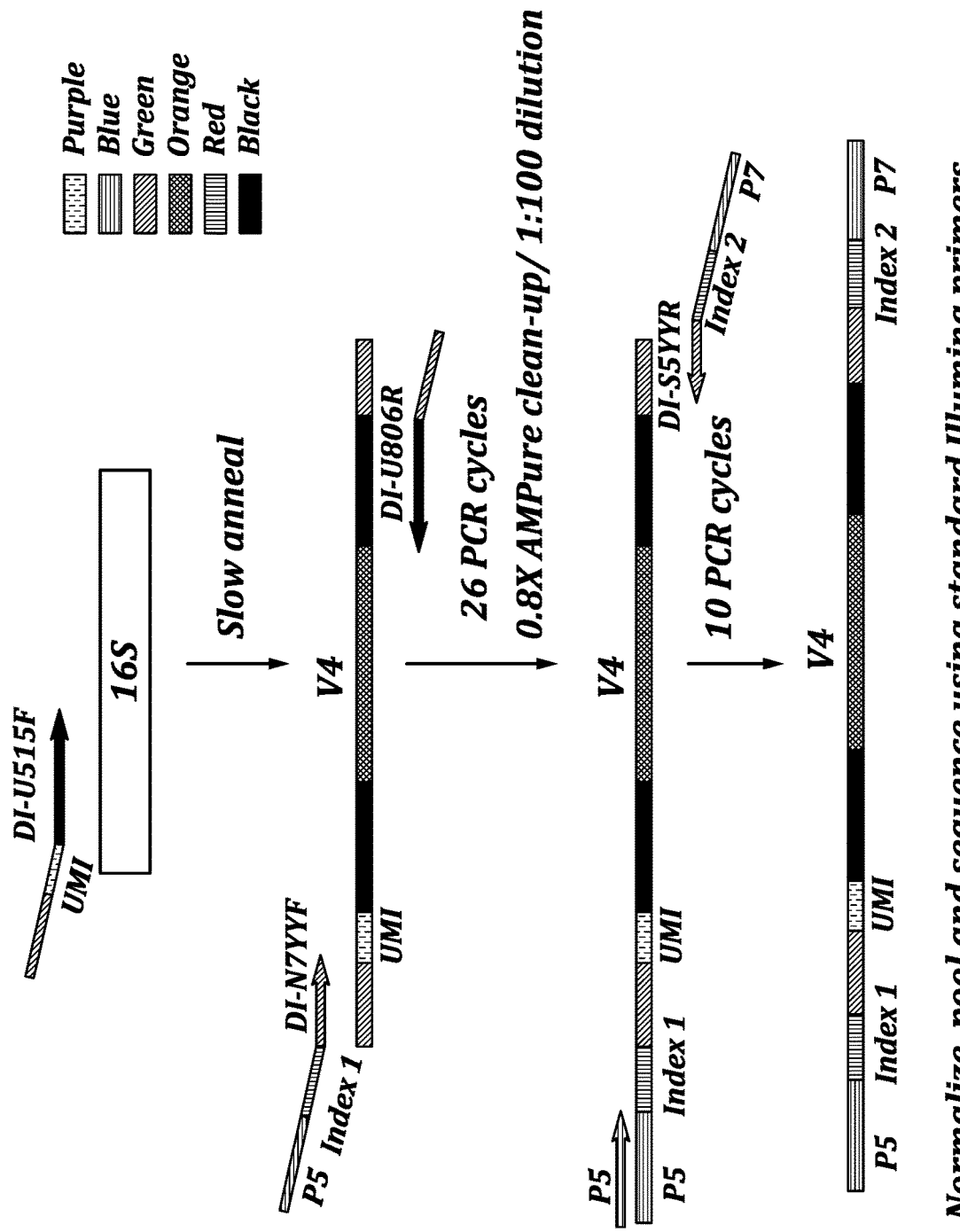
FIGS. 1A and 1B schematically illustrate two representative strategies for incorporating UMI into a taxonomically relevant amplicon.

The approach described herein is an improvement on standard PCR methods to amplify and sequence genetic targets (e.g., including taxonomic markers such as variable regions of 16S that exhibit diversity within a heterogeneous sample pool). The approach allows for improved profiling, avoidance of overrepresentation due to amplification bias, and detection of chimeras. The approach can be applicable to improved quantitation of disease-associated taxa in the microbiota and environmental samples, and can be used to better target specific communities or segments thereof as part of microbial-directed therapeutic approaches. The disclosed approaches can leverage more economical sequencing approaches (e.g., MiSeq®) and maintain optimized throughput levels that exist for amplicon sequencing.

In one aspect, the disclosure provides a method for generating a library for the detection of one or more operational taxonomic units (OTUs) in a heterogenous (i.e., mixed) microbial population.

As used herein, the term operational taxonomic unit (OTU) refers to an identifiable organism (e.g., microorganism) that is distinct from other and potentially closely related microorganism. The term is a pragmatic proxy for the term "species" for microorganisms and is based on identifiable variations in relevant genetic markers, also referred to herein as a "taxonomically relevant genomic sequence." Taxonomically relevant genomic sequences are genetic markers that are known to accrue genetic mutations over time at a sufficiently constant rate such that a measurement of genetic total difference and/or taxonomic relationship between organisms can be inferred from the genetic differences observed in each organism's respective taxonomically relevant genomic sequence. Preferred taxonomically relevant genomic sequences in the context of this disclosure are ones that can be detected or amplified using reagents that leverage sufficiently conserved sequences among the diversity of microorganisms adjacent or near to the taxonomically relevant genomic sequence such that the taxonomically relevant genomic sequence can be amplified from each microorganisms regardless of the ultimately assigned OTU. Illustrative, non-limiting examples of taxonomically relevant genomic sequence include hypervariable regions of the 16S rRNA gene (for prokaryotes), hypervariable regions of the 18S rRNA gene (for eukaryotes) and the Internal Transcribed Spacer region (for eukaryotes), or portions thereof. For example, the 16S rRNA gene contains nine hypervariable regions (V1-V9). Any one of such variable regions, or a portion thereof, can be informative as to designating an OTU and, thus, can be considered a taxonomically relevant genomic sequence in the context of this disclosure.

In this aspect, the method comprises a step of adding at least one Unique Molecular Identifier (UMI) to the target taxonomically relevant genomic sequence to be analyzed prior to amplification that is subsequently accomplished in multiple rounds of PCR. Additional index barcodes can be later added during the amplification cycles. As used herein, the term "Unique Molecular Identifier" (UMI), refers to unique, variable length sequences that can tag the starting template molecule that is to be subsequently copied or amplified to facilitate sequencing and analysis. The use of UMI can help overcome the quantitation challenge introduced when copying DNA or RNA molecules and facilitates the accurate quantitation of original taxonomically relevant genomic sequence and OTU profiling. In contrast, as used herein the term "index" refers to a nucleic acid tag or barcode that is introduced to the target sequence during or after the amplification process. These index sequences provide a common tag to all of the amplicons generated in a particular sample and can serve to distinguish amplicons generated from distinct samples or subsamples that were initially separate. These index sequences can be useful when multiple samples undergo initial tagging with unique UMI but are later pooled for high-throughput amplification and/or sequencing. Alternatively, multiple experiments can be tracked and compared using the index tags to identify the particular sample or batch. More detail regarding potential designs of the UMI and index sequences is provided below.

The method encompasses embodiments where either one or two UMI domains are added to the target taxonomically relevant genomic sequence prior to amplification.

In an exemplary embodiment of the single UMI approach, the method comprises contacting a sample containing nucleic acids obtained from a heterogeneous microbial population with a first tagging polynucleotide primer. As used herein, the terms "nucleic acid", "polynucleotide", "nucleotide", and "oligonucleotide" can be used interchangeably to nucleic acid comprising DNA, RNA, derivatives thereof (e.g., xenonucleic acids (XNA), made with synthetic nucleic acids and capable of information storage like DNA or RNA), or combinations thereof. The molecules can comprise canonical nucleic acid bases (i.e., adenine, cytosine, guanine, thymine (or uracil for RNA) or non-canonical bases. Unless defined specifically otherwise, the terms "nucleic acid", "polynucleotide", "nucleotide", and "oligonucleotide" can refer to single stranded or double stranded molecules.

The first tagging polynucleotide is a single stranded nucleic acid (e.g., ssDNA, ssRNA, or ssXNA) and typically comprises multiple domains: a domain at the 3'-end with a sequence that specifically anneals to, or anneals near to, a taxonomically relevant genomic sequence in the microbial population; a unique molecular identifier (UMI) sequence domain; and a first linker sequence, as set forth in the following scheme:

5'-[Linker]-[UMI]-[specific annealing sequence]-3'

This exemplary format is illustrated in FIG. 1A, which shows at the top a first tagging polynucleotide primer. The 3' annealing domain is a black arrow labeled with "DI-U515F", which refers to the sequence that anneals to the 16S target region. The UMI domain is designated as purple, and the first linker sequence is labelled as green. The UMI domain is disposed between the first linker sequence and the sequence that specifically anneals to, or anneals near to, a 16S V4 hypervariable sequence in the microbial population.

The linker sequence can be any target sequence that provides a template to which later primers can anneal to facilitate amplification in subsequence PCR steps. This linker is typically universal to (i.e., conserved among) all of the individual primers used together in a single processing batch.

In the context of a plurality or batch of first tagging polynucleotide primers that are typically used in aggregate to tag multiple starting genomic molecules in the sample, the UMI domain is or comprises a degenerate sequence. In this regard, some or all of the positions in the domain vary in the identity of the base that occupies that position. Thus, each individual in the aggregate is highly likely to be unique and distinguishable from the other species in the aggregate. Accordingly, unless stated otherwise, references here to the UMI domain invokes the domain itself that contains degeneracies or regions of degeneracy, whereas reference to a particular UMI sequence refers to a specific individual that, in isolation, is not degenerate but has a highly unique primary sequence and is distinguishable from the majority of the other species in the batch. The entire UMI domain is not necessarily degenerate, but instead the domain can have variable interspersed constant bases that create sub-regions of degeneracy (for example, NNNANTNNNGNNN; set forth as SEQ ID NO:1). In some embodiments, the UMI domain can be at least about 50%, about 55%, about 60%, about 65%, about 70%, about 75%, about 80%, about 85%, about 90%, about 95%, and 100% degenerate.

The degenerate positions in the UMI domain can have random distributions of the canonical and noncanonical nucleotide bases. In other embodiments, the distribution of canonical and noncanonical nucleotide bases at any given degenerate position might be biased. For example, the GC content may be skewed. In some embodiments, the GC content of any one or more degenerate position in the UMI domain, or indeed the entire UMI domain itself, can be about 70%, about 65%, about 60%, about 55%, about 50%, about 45%, about 40%, about 35%, about 30%, about 25%, about 20%, or any intermediate percentage. An illustrative range is between about 50% and about 20% GC content. An alternative illustrative range is between 40% and about 30% GC content.

The UMI domain can have variable lengths. In some embodiments, the UMI domain is between 5 and 100 nucleotides in length, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nucleotides, although the domain need not be limited as such and the disclosure contemplate UMI domains that are longer. In some embodiments, the UMI can be about 5 to about 150 nucleotides in length, about 5 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, or about 5 to about 10 nucleotides in length and all oligonucleotides intermediate in length of the sizes specifically disclosed to the extent that the oligonucleotide is able to achieve the desired result. In one embodiment, the UMI can be about 7 to 15 nucleotides in length.

Referring to the domain containing the sequence that specifically anneals to or anneals near to a taxonomically relevant genomic sequence, this sequence is typically universal (i.e., non-degenerate) and is shared among all of the individual primers used together in a single processing batch. As used herein, term "specifically anneals" refers to the ability of the indicated single stranded domain to form hydrogen bonds with a template or target nucleic acid sequence sufficient to maintain a double-stranded configuration such that the oligonucleotide can be extended via polymerase action across the target taxonomically relevant genomic sequence as the template. This requires a threshold level of sequence complementarity between this annealing domain of the first tagging polynucleotide primer and the target genomic sequence to ensure sufficiently strong base pairing and avoid non-specific binding to other sequences under standard reaction conditions. The annealing domain sequence can be rationally designed for any appropriate taxonomically relevant genomic sequence of choice, typically targeting a conserved region that is near or adjacent to a hypervariable region of interest that will serve to inform OTU classification. For example, illustrative, non-limiting annealing sequences configured to tag and the V4 and other hypervariable domains of the 16S rRNA gene are provided below in Table 1. As presented, the illustrative annealing domains are in forward and reverse pairs. It will be understood, however, that the domains need not be paired in corresponding forward and reverse primer pairs. Instead, in the single UMI approach disclosed herein, the first tagging polynucleotide would only contain a single exemplary annealing sequence and no corresponding tagging polynucleotide would be utilized for a UMI tagging polynucleotide.

TABLE 1

Exemplary annealing domains for tagging the indicated hypervariable regions of 16S rRNA gene.

| V4 | |
|---|---|
| F (515F): GTGCCAGCMGCCGCGGTAA | SEQ ID NO:2 |
| R (806R): GGACTACHVGGGTWTCTAAT | SEQ ID NO:3 |
| F (515F): GTGYCAGCMGCCGCGGTAA | SEQ ID NO:4 |
| R (806R): GGACTACNVGGGTWTCTAAT | SEQ ID NO:5 |
| V1-V3 | |
| F (27F): AGAGTTTGATCNTGGCTCAG | SEQ ID NO:6 |
| R (519R): GTNTTACNGCGGCKGCTG | SEQ ID NO:7 |
| F (27F): AGAGTTTGATCCTGGCTCAG | SEQ ID NO:8 |
| R (534R): ATTACCGCGGCTGCTGG | SEQ ID NO:9 |
| V6-V8 | |
| F (926F): AAACTYAAAKGAATTGACGG | SEQ ID NO:10 |
| R (1392R): ACGGGCGGTGTGTRC | SEQ ID NO:11 |
| V1-V4 | |
| F (27F): AGAGTTTGATCNTGGCTCAG | SEQ ID NO:12 |
| R (806R): GGACTACHVGGGTWTCTAAT | SEQ ID NO:13 |
| F (27F): AGAGTTTGATCNTGGCTCAG | SEQ ID NO:14 |
| R (806R): GGACTACNVGGGTWTCTAAT | SEQ ID NO:15 |
| V3-V4 | |
| F (314F): CCTACGGGNGGCWGCAG | SEQ ID NO:16 |
| R (805R): GACTACHVGGGTATCTAATCC | SEQ ID NO:17 |

TABLE 1-continued

Exemplary annealing domains for tagging the indicated hypervariable regions of 16S rRNA gene.

V3-V5

| | |
|---|---|
| F (357F): CCTACGGGAGGCAGCAG | SEQ ID NO:18 |
| R (926R): CCGTCAATTCMTTTRAGT | SEQ ID NO:19 |

V1-V9

| | |
|---|---|
| F (27F): AGAGTTTGATCNTGGCTCAG | SEQ ID NO:20 |
| R (1492R): CGGTTACCTTGTTACGACTT | SEQ ID NO:21 |

To facilitate annealing of the tagging polynucleotide primer to all variants of the potential target nucleic acid molecules, conditions are provided to increase the stringency of the reaction to facilitate enhanced specificity of the tagging polynucleotide primer to the intended annealing site on or near the target nucleic acid molecules. This increase stringency can be accomplished by increasing the salt concentrations in the annealing reaction. The salt concentrations can, for example, be increased gradually over time to reduce the likelihood of non-specific binding. Alternatively or additionally, tagging polynucleotide primer can comprise one or more locking nucleic acids (LNAs) configured according to common skill in the art to enhance binding specificity of the tagging polynucleotide primer to the locus at or near to the taxonomically relevant genomic sequence. For example, the tagging polynucleotide primer can be configured to comprise 1, 2, 3, 4, 5, 6, 7, 8, 9, 10 or more LNAs.

In some embodiments a prolonged and gradual annealing phase can be employed. For example, the sample can be heated to a typical "melting" temperature to denature the target microbial nucleic acid molecules and disrupt molecule to molecule associations resulting in single stranded molecules. A typical melting temperature is between 90° C. and 99° C., such as about 97° C. or 98° C. After a sufficient period of time to achieve acceptable melting or denaturization, the sample (containing the (first) tagging polynucleotide primers) is slowly and gradually cooled to allow the tagging polynucleotide primer to specifically anneal to a target nucleic acid. For example, embodiments include cooling the sample (containing the (first) tagging polynucleotide primers) at a rate of less than about 0.5° C. per second, about 0.4° C. per second, about 0.3° C. per second, about 0.2° C. per second, about 0.1° C. per second, or slower. The cooling at any of these rates can be for at least 1, 2, 3, 4, 5, 6, 7, 8, 9, 10, 11, 12, 13, 14, 15, or more minutes. This cooling step can be performed to achieve a final temperature of about 65° C., about 60° C., about 55° C., about 50° C., about 45° C., about 40° C., about 35° C., about 30° C., about 25° C., about 20° C., or lower, which is held until the next phase of the method (e.g., amplification) is performed.

For example, in one embodiment, this cooling step comprises cooling the sample from the initial melting temperature at a substantially linear rate of less than 0.5° C. per second for at least one minute. In another embodiment, the sample is cooled from an initial melting temperature at a substantially linear rate of 0.3° C. or less per second for at least 3 minutes. In another embodiment, the sample is cooled from an initial melting temperature at a substantially linear rate of 0.3° C. or less per second for at least 4 minutes. In another embodiment, the sample is cooled from an initial melting temperature at a substantially linear rate of 0.3° C. or less per second for at least 4.5 minutes. In another embodiment, the sample is cooled from an initial melting temperature at a substantially linear rate of 0.2° C. or less per second for at least 4 minutes. In another embodiment, the sample is cooled from an initial melting temperature at a substantially linear rate of 0.2° C. or less per second for at least 4.5 minutes. In another embodiment, the sample is cooled from an initial melting temperature at a substantially linear rate of 0.2° C. or less per second for at least 5 minutes. In another embodiment, the sample is cooled from an initial melting temperature at a substantially linear rate of 0.2° C. or less per second for at least 6 minutes. In another embodiment, the sample is cooled from an initial melting temperature at a substantially linear rate of 0.1° C. or less per second for at least 4 minutes. In another embodiment, the sample is cooled from an initial melting temperature at a substantially linear rate of 0.1° C. or less per second for at least 6 minutes. In another embodiment, the sample is cooled from an initial melting temperature at a substantially linear rate of 0.1° C. or less per second for at least 8 minutes. In another embodiment, the sample is cooled from an initial melting temperature at a substantially linear rate of less than 0.1° C. per second for at least 10 minutes. In another embodiment, the sample is cooled from an initial melting temperature at a substantially linear rate of 0.1° C. or less per second for at least 12 minutes.

In combination with the level of degeneracy of the UMI domain, the concentration of the first tagging polynucleotide primer can affect the likelihood that any particular UMI sequence is tagged to initial target taxonomically relevant sequences. Thus, in some embodiments, the first tagging polynucleotide primer is contacted to the sample at a final sample concentration of about 100 pM, 75 pM, 50 pM, 25 pM, 20 pM, 15 pM, 10 pM, or 5 pM, or any concentration in between.

As indicated above, either one or two UMI domains can be added to (i.e., "tagged" to) the target taxonomically relevant genomic sequence prior to amplification.

Thus, in other embodiments, a dual UMI approach can be used that comprises contacting the sample containing nucleic acids obtained from a heterogeneous microbial population with a first tagging polynucleotide primer and a second tagging polynucleotide primer. This approach results in a first and second UMI sequence tagged at either side of the taxonomically relevant genomic sequence. The presence of two UMI tags adds additional complexity to the possible UMIs assigned to single molecules. Moreover, dual UMI tagging provides an additional utility to be able to readily detect when a chimera has formed during amplification or sequencing, as discussed in more detail below.

The first and second tagging polynucleotide primers are as described above in the context of the exemplary single UMI approach. The specific annealing sequences for each of the first and second tagging polynucleotide primers, however, are distinct and each rationally designed to anneal to locations on the target genomic sequences that are adjacent to or flank opposing sides of the taxonomically relevant genomic sequence. In this sense, the first and second tagging polynucleotide primers can be considered forward and reverse primers, such disclosed in Table 1 above.

Figure 10:
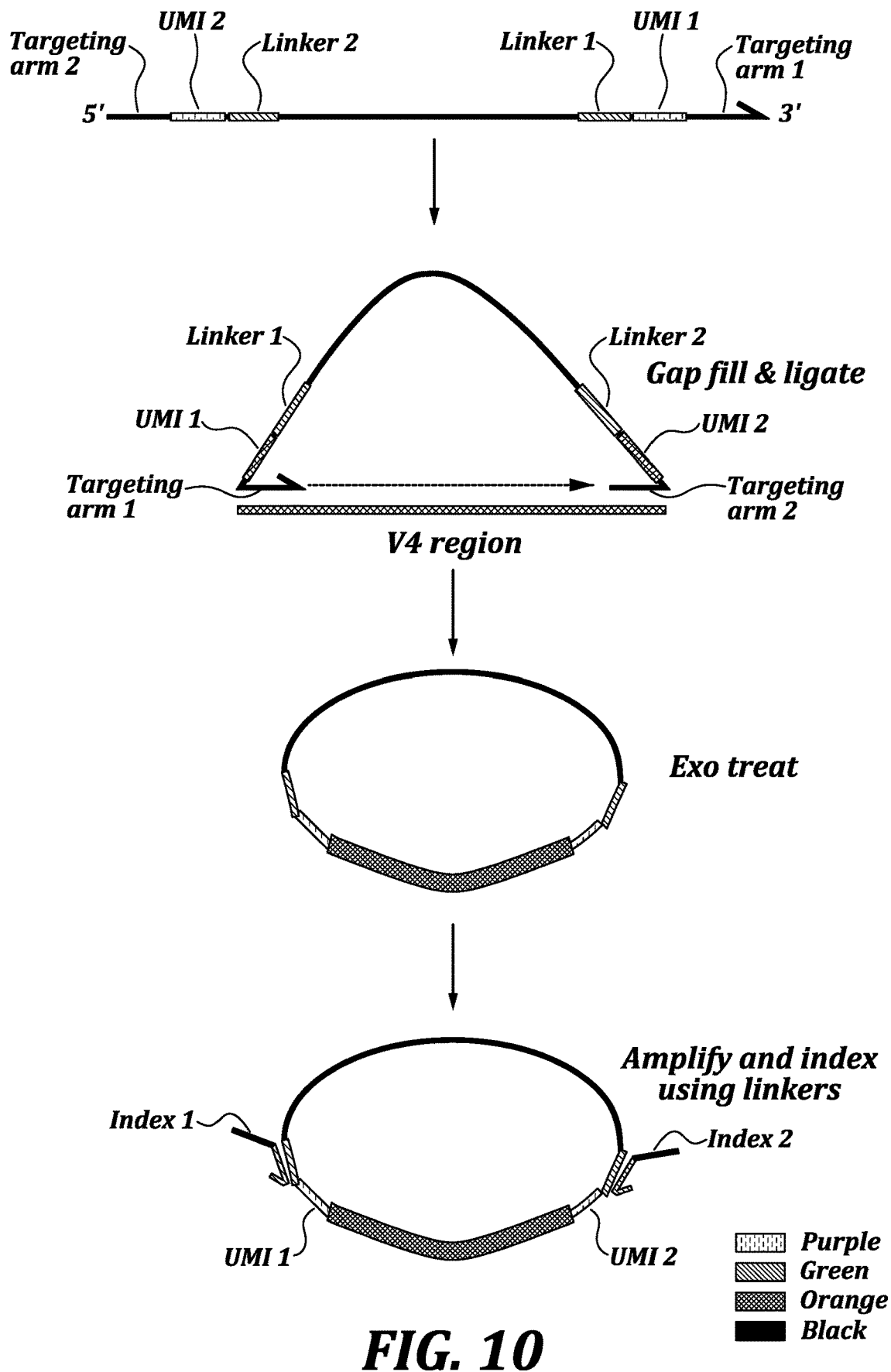
FIG. 10 schematically illustrates use of a molecular inversion probe to implement a dual UMI approach such that a UMI is incorporated on either side of the taxonomically relevant genomic sequence.

In yet other embodiments, a dual UMI approach can be used wherein the first tagging polynucleotide and second tagging polynucleotide are each part of the same molecular inversion probe that is contacted to the sample. A molecule inversion probe can greatly enhance the rate of incorporation of a UMI sequence at the intended locations flanking either side of the desired taxonomically relevant genomic sequence because the independent incorporation of two such UMI domains can be a low probability event when the tagging polynucleotides (containing the UMI domains) are used in low concentration. Referring to FIG. 10 illustrating a specific embodiment, the first tagging polynucleotide (with a first linker sequence, first UMI domain, and first targeting arm that anneals to or near to the taxonomically relevant genomic sequence) and second tagging polynucleotide (with a second linker sequence, second UMI domain, and second targeting arm that anneals to or near to the taxonomically relevant genomic sequence) are at opposite ends of the single molecular inversion probe. The domains that specifically anneal to the target genomic sequence do not act as a forward and reverse primer pair per se, because they each hybridize to the same single stranded template molecule (here at or near the 16S V4 sequence). Thus, one of the tagging polynucleotides does not serve strictly as a primer that could initiate extension by a polymerase. The annealing sequence of only one of the tagging polynucleotide (e.g, the first targeting arm) is at the 3'-end of the inversion probe primes the extension via polymerase along the taxonomically relevant genomic sequence as a template. The extension continues until the polymerase runs into the annealed sequence from the other tagging polynucleotide (e.g., targeting arm 2), which is at the 5'-end of the inversion probe. A ligation event connects the extended 3'-end to the annealing sequence of the 5'-end, thus resulting in a circularized nucleic acid that comprises (from 5' to 3') the linker sequence, the UMI sequence and the target specific annealing sequence of one of the tagging polynucleotides (e.g., the first tagging polynucleotide), followed by the sequence (or reverse complement thereof) of the taxonomically relevant genomic sequence, which is further followed by the target specific annealing sequence, the UMI sequence, and the linker sequence of the other tagging polynucleotides (e.g., the second tagging polynucleotide). This construct can then be used for as a template for further amplification using separate first tagging polynucleotide and second tagging polynucleotide molecules as primers, or alternatively using universal primers that can anneal to the linker sequences incorporated into the circularized template on either side of the two UMI domains. The circularized template can optionally be linearized at a location that preserves the first tagging polynucleotide and second tagging polynucleotide sequences in their flanking orientations relative to the taxonomically relevant genomic sequence.

Whether using a single or dual UMI approach, as described above, the method can also comprise a step of extending the annealing sequence at the 3'-end of the tagging polynucleotide primer along the target genomic molecule to include the sequence (or reverse complement thereof) of the taxonomically relevant genomic sequence. This can be accomplished by the inclusion of an appropriate polymerase with the routine inclusion of dNTPs, buffer, appropriate cations, and the imposition of appropriate extension conditions to facilitate the polymerase action as known in the art.

After the at least one Unique Molecular Identifier (UMI) is tagged to the target taxonomically relevant genomic sequence, amplification is subsequently accomplished in multiple rounds of PCR cycling. In some embodiments, the amplification step comprises contacting the sample with a first indexing primer and a second indexing primer. As described in more detail above and below, the indexing primers contain index sequences that provide a common barcode to all of the molecules amplified in the same batch reaction. The index sequences in the first and second indexing primers are typically different from each other. In some embodiments, the first indexing primer and the second indexing primer are not used in the same amplification cycling rounds, but instead are applied in two separate amplification stages. This is referred to as a "two-stage dual indexing" and a schematic of an exemplary embodiment thereof is illustrated in the lower portion of FIG. 1A.

In the first stage after the initial contacting with the first tagging polynucleotide (and, e.g., the slow anneal stage), the new template is contacted with a first indexing primer. The first indexing primer has a domain (labeled as a green arrow) that anneals to the first linker sequence (labeled as a green domain) that was incorporated previously by the first tagging polynucleotide. The first indexing primer also has a first indexing domain ("index 1"; labeled as red) and a first universal primer annealing domain (here, specifically for P5; blue). The first indexing primer acts as a forward primer in conjunction with a reverse primer that comprises a second linker sequence (labeled as green) and a domain (indicated with "DI-U806R"; labeled as black) with a sequence that anneals to a target nucleic acid that flanks the taxonomically relevant genomic sequence at the side opposite from the first indexing primer. Exemplary sequences that can be incorporated as annealing domains in the reverse primer are provided in above in Table 1 for select regions of the 16S rRNA gene. These primers are used to produce a first plurality of amplicons when the sample is subjected to the appropriate cycling conditions and PCR reagents as generally understood in the art. Typically, this first amplification stage incorporates between about 18-30 cycles, such as about 20, 21, 22, 23, 24, 25, 26, 27, 28, 29, or 30 cycles. In some embodiments, the first amplification stage incorporates between about 20-30 cycles, 22-28 cycles, 24-28 cycles, or 26-28 cycles. After the first stage of amplification, the reaction sample with the first plurality of amplicons can be cleaned up to remove unused reagents and the like.

In the second stage, the first plurality of amplicons is contacted with the second indexing primer (see FIG. 1A). The second indexing primer has a domain (labelled as a green arrow) that anneals to the second linker sequence incorporated by the reverse primer in the proceeding first stage amplification. The second indexing primer also has a second indexing domain ("index 2"; labeled as red) and a second universal primer annealing domain (here, specifically for P7; labeled as blue). The second indexing primer and a universal primer (here "P5"; labeled as blue) together act as forward and reverse primers that produce a second plurality of amplicons after several rounds of amplification. The second stage typically has fewer rounds of amplification as the first round, such as about 5-15 cycles. For example, the second stage can have 5, 6, 7, 8, 9, 10, 11, 12, 13, 14, or 15 cycles. In some embodiments, the second amplification stage incorporates between about 5-14 cycles, 7-12 cycles, 9-12 cycles, or 10-11 cycles. After the second stage of amplification, the reaction sample with the second plurality of amplicons can be cleaned up to remove unused reagents and the like.

In some embodiments, the first indexing primer and the second indexing primer are used as forward and reverse primers in the same amplification cycling rounds to provide a single amplification stage. This is referred to as a "one-" or "single-stage dual indexing" and a schematic of an exemplary embodiment thereof is illustrated in the lower portion of FIG. 1B. In the illustrated embodiment, each of the first and second indexing primers maintains the same structure as described above. The second indexing primer, specifically, has a domain ("DI-US5YYR"; labelled as green) that anneals to the second linker sequence domain (labelled as green) that was previously incorporated by a second tagging polynucleotide primer in a dual UMI tagging step. If only a single UMI tagging step precedes the amplification step, the second indexing primer can instead contain a 3'-end domain with a sequence that specifically anneals to a location that flanks or is near the target taxonomically relevant genomic sequence on the side opposite of the first indexing primer (and the first tagging polynucleotide primer.)

In view of the above, the method can comprise any combination of dual UMI or single UMI tagging with dual indexing, with the dual indexing accomplished in a single stage or two-stage process. More specifically, the method can comprise a dual UMI, single stage dual index process; a dual UMI, two-stage dual index; a single UMI, two-stage dual index; or a single UMI, single stage dual index. For example, in one illustrative embodiment, the method comprises a single UMI, two-stage dual index approach for generating the library. Such an illustrative embodiment can comprise the following steps:

contacting a sample comprising nucleic acids obtained from the heterogeneous microbial population with a first tagging polynucleotide primer, wherein the first tagging polynucleotide primer comprising a unique molecular identifier (UMI) sequence domain disposed between a first linker sequence and a sequence at the 3'-end that specifically anneals to, or anneals near to, a taxonomically relevant genomic sequence in the microbial population;

providing conditions to allow the first tagging polynucleotide primer to specifically anneal to a target nucleic acid in the sample at or near to the taxonomically relevant genomic sequence; and amplifying the taxonomically relevant genomic sequence to provide a plurality of amplicons comprising the first tagging polynucleotide primer sequence and the taxonomically relevant genomic sequence. The approach can further comprise steps of sequencing a segment of the amplicons comprising the first tagging polynucleotide primer sequence and the taxonomically relevant genomic sequence. Additionally, the approach can further comprises assigning the sequenced amplicons to one or more OTUs based on the determined taxonomically relevant genomic sequence. It will be understood that these additional elements, such as sequencing and assigning sequences to one or more OTUs can similarly be applied to any other format contemplated in this disclosure.

In some embodiments, the method comprises preparing the sample comprising nucleic acids obtained from a microbial population. For example, using commonly known techniques, members of the microbial population can be lysed and the nucleic acids extracted to provide the sample.

The microbial population can be obtained from any relevant source of interest, such as an environmental sample or biological sample. Biological samples can include bodily fluids, swabs from skin, cavity or nares, excretions (e.g., fecal samples), or result from biopsies, and the like.

In another aspect, the disclosure provides a method for detecting one or more operational taxonomic units (OTUs) in a heterogeneous microbial population. Detecting one or more OTUs can include detecting the relative abundance or absolute abundance of the one or more OTUs in the heterogeneous microbial population or sample. As described herein, the disclosed method provides for increased accuracy for determination of the abundance of the OTUs in part because the method reduces or eliminates amplification bias during the generation and sequencing of the libraries. The method comprises generating the library as described above, and further comprises sequencing at least a portion of the resulting plurality of amplicons (e.g., in some described embodiments referred to the "second plurality of amplicons" to produce multiple sequences for analysis. Each sequence can correspond to the entire length of the amplicon or can correspond to a fragment of the each amplicon. Preferably, the sequence includes at least a UMI sequence and the taxonomically relevant genomic sequence from the amplicon. In some embodiments, the determined sequence comprises two UMI sequences flanking either end of the taxonomically relevant genomic sequence. In some embodiments, the determined sequence further comprises at least one or both indexing sequences.

The resulting sequences can be further subject to analysis, e.g., to ascertain the representation of one or more OTU in the initial microbial population based on the determined taxonomically relevant genomic sequences. Operational taxonomical units in a sample can be established by mapping each sequenced amplicon to databases of known species or taxa at a certain identity threshold. For example, to define species level taxa OTUs reads can be mapped at, e.g., 97% sequence identity (ID) across the complete read. In some embodiments, the reads are further deduplicated after mapping each read to an OTU. An OTU with multiple reads that share duplicate UMIs are collapsed into a single representative read. The term duplicate UMIs include UMIs that have the same sequence (i.e., share 100% sequence identity) or similar UMIs within a set threshold for similarity (e.g., with at least 95% sequence identity in the UMI sequences.) This deduplication process improves the accuracy of quantitating original representation in the microbial population because it reduces or eliminates the PCR/amplification bias that can occur during PCR. This permits better quantitation of unique read counts and helps flag chimeras for elimination. In some embodiments, the UMIs in an assigned OTU are deduplicated (i.e., collapsed into a single representative read) if the UMIs share at least about 95%, 96%, 97%, 98%, 99%, or 100% sequence identity as defined according to standard criteria in the art. In one embodiment, the UMIs in an assigned OTU are deduplicated (i.e., collapsed into a single representative read) if the UMIs share at least 97% sequence identity.

In another aspect, the disclosure provides a method for detecting a nucleic acid chimera that forms during the generation of a sequencing library. Unless specifically addressed below, elements of the sequencing library can be developed similarly as generally described above for the dual tagging approaches. After first and second UMI domains have been incorporated, each on an opposite side of the target nucleic acid sequence, the amplicons are generated with a single or dual-stage indexing strategy that ultimately incorporates additional universal annealing sites and index barcodes on either end of the amplicon. These are used to sequence the amplicons in any preferred method of sequencing. The sequences are assessed for the presence of the first and second UMI sequences at either end of the target nucleic acid sequence. A chimera is indicated when the sequences of the first and/or second UMI sequence domain are discordant with other UMI domain pairs for that molecule. In this regard, a chimera may have a pair of UMI where one of the UMI sequences does not match or deduplicate with the corresponding UMI sequences in reads in the same OTU. In some embodiments, the lack of one or more UMI sequence indicates that the sequence is a chimera. In some instances, these chimeric sequences are flagged for removal from the sequence dataset.

While the present disclosure contemplates and encompasses embodiments that are employed towards any target nucleic acid sequence of interest, the below descriptions are discussed specifically in the context of construction, sequencing, and analysis of libraries that are directed to taxonomically relevant genomic sequences for the ultimate analysis of, e.g., metagenomic structure in a heterogeneous population.

Figure 1B:
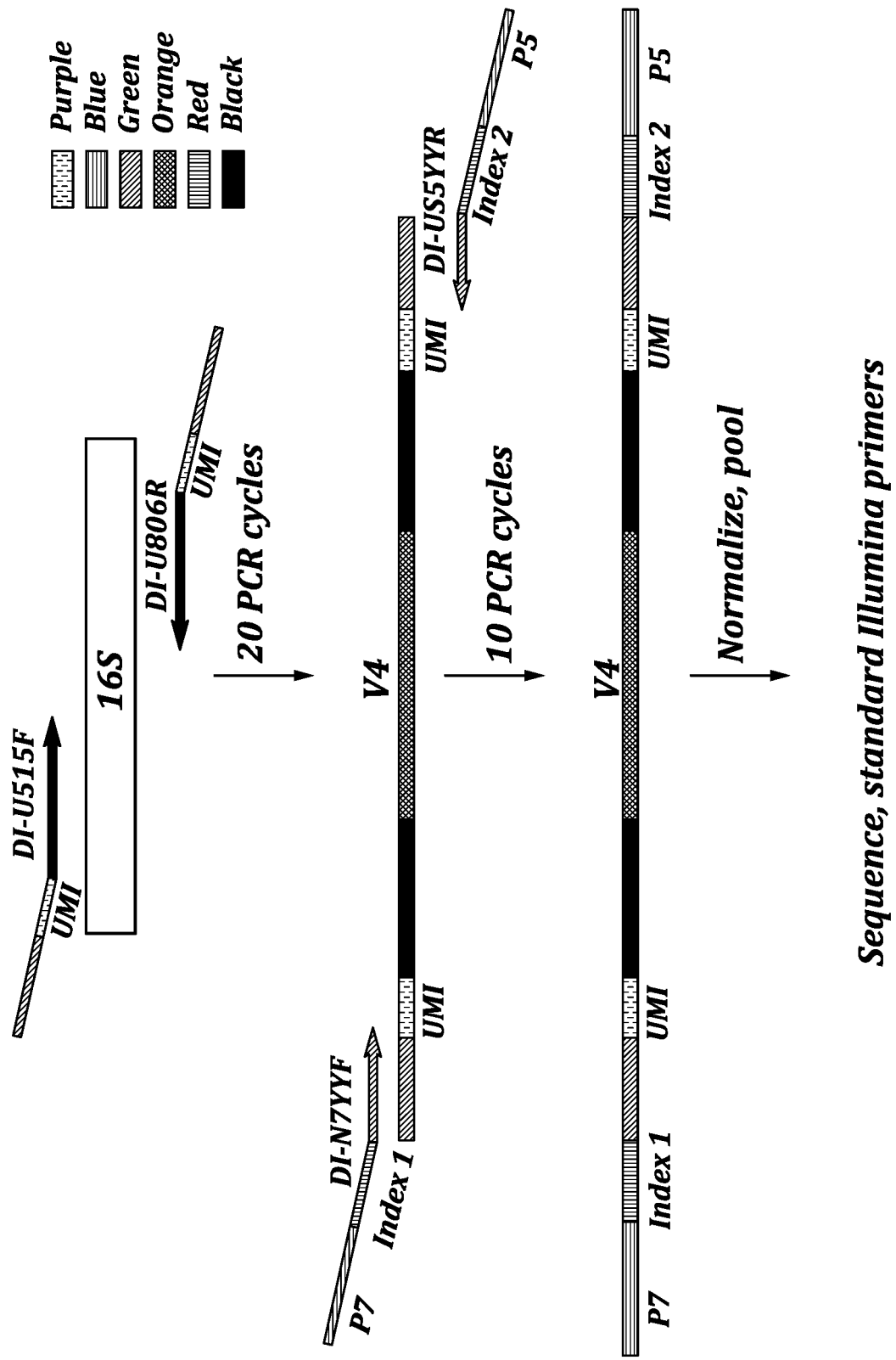

In some exemplary embodiments, the method comprises contacting a sample comprising nucleic acids from a heterogeneous microbial population with a first tagging polynucleotide and a second tagging polynucleotide that specifically anneal to either side of a taxonomically relevant genomic sequence in the microbial population. One exemplary format is illustrated in FIG. 1B, which shows at the top a first tagging polynucleotide primer and a second tagging polynucleotide primer annealing to the target 16S rRNA genetic template via the first and second targeting domains, respectively (each labeled as black arrows). The first tagging polynucleotide and the second tagging polynucleotide comprise a first unique molecular identifier (UMI) sequence domain second unique molecular identifier (UMI) sequence domain, respectively (each labeled as purple), as well as a first and second linker annealing domain, respectively (each labeled as green).

The method further comprises amplifying the taxonomically relevant genomic sequence in a first stage to produce a first plurality of amplicons that, assuming an error free reaction, would each incorporate the first UMI and second UMI sequence at either end of the target taxonomically relevant genomic sequence. In some embodiments, the first stage of amplification utilizes the first tagging polynucleotide and the second tagging polynucleotide as primers for multiple cycles of amplification. In other embodiments, forward and reverse primers are used that are configured to specifically anneal to portions of sequence (e.g., linker sequences) incorporated by the first tagging polynucleotide and the second tagging polynucleotide.

Next, the first plurality of amplicons is contacted with a first indexing primer and a second indexing primer. As described above, and illustrated in FIG. 1B, the first indexing primer and a second indexing primer is configured to specifically anneal in standard cycling conditions to the first linker annealing sequence and second linker annealing sequence, respectively, that were incorporated previously by the tagging polynucleotides (these domains are labeled as green for continuity). The first indexing primer and a second indexing primer also comprise a first and second index barcode, respectively, and a first and second universal primer annealing sequence at the respective 5'-ends. Using the first and second indexing primers as forward and reverse primers, the additional rounds of PCR cycling are performed in a second amplification stage to produce a second plurality of amplicons. Assuming an error free reaction, each of the second plurality of amplicons comprise the first universal primer annealing sequence, the first index sequence, a first UMI sequence, the taxonomically relevant genomic sequence, a second UMI sequence, the second index sequence, and the second universal primer annealing sequence. In at least a portion of the plurality of the second amplicons, the method comprises sequencing the amplicons with universal primers that anneal to the first and second universal primer annealing sequences. Ultimately, a chimera is detected when the sequences of the first and/or second UMI sequence domain are discordant with other UMI domain pairs for that molecule. In some embodiments, a chimera is detected when the sequences of the first or second UMI sequence domain is not detected or is not present in a resulting single sequence. The sequence can be flagged for removal from the data set. In cases of metagenomics analyses, the sequence would not be assigned to an OTU.

In further embodiments, the first stage of amplification (i.e., using the first and second tagging polynucleotides as primers) comprises at least about 15 rounds of PCR cycling. For example the first stage of amplification can comprise 15, 16, 17, 18, 19, 20, 21, 22, 23, 24, 25 or more rounds of cycling. In further embodiments, embodiments, the second stage of amplification comprises between about 5 and 15 rounds of PCR cycling. For example the second stage of amplification (i.e., using indexing primers) can comprise 5, 6, 7, 8, 9, 10, 11, 12, 13, 14, or 15 rounds of cycling. Persons of ordinary skill in the art can readily determine acceptable cycling conditions and reagents appropriate for this purpose. Optimized conditions and reagent mixtures are described elsewhere in this disclosure.

In alternative embodiments, the initial steps of incorporating the first and second UMI are performed using a molecular inversion probe approach, as described above and illustrated in FIG. 10. Briefly, the first and second tagging polynucleotides are incorporated at opposite ends in the same single stranded molecule. The tagging polynucleotides are configured such that the respective first and second targeting arms that anneal to the target genomic molecule sequence are that the 3'- and 5'ends, respectively. In some embodiments, a first amplification stage can comprise a slow and gradual annealing phase can be employed, as described elsewhere herein. The first annealing domain at the 3'-end of the probe serves as a primer allowing polymerase-driven extension across the taxonomically relevant genomic sequence up to the 5'-end of the annealed second tagging polynucleotide. The 3'-end of the extended first tagging polynucleotide is ligated to the 5'-end of the second tagging molecular polynucleotide to provide a circularized single stranded molecule. This circularized single stranded molecule serves as the template for further amplification, indexing to provide amplicons amenable to sequencing. The reaction can be exposed to exonuclease treatment to remove all linear nucleic acid molecules, leaving only the circularized molecules. In some embodiments, there is no further amplification in this stage. In other embodiments, the first amplification stage further comprises additional rounds of amplification using forward and reverse primers that are configured to specifically anneal to portions of sequence (e.g., linker sequences) incorporated into the circular molecule by the first tagging polynucleotide and the second tagging polynucleotide.

The first stage is followed by a second stage using indexing primers that specifically anneal to the linker annealing sites. The structures of the individual tagging polynucleotides and indexing primers are described above. The number of rounds for each stage can be as described above. Alternatively, the further amplification can proceed in a single stage merely using first and second indexing primers that specifically anneal to the first and second linker annealing sites incorporated in the molecular inversion molecule. This single stage can comprise between 15 and 30 or more rounds of PCR amplification using standard cycling conditions or optimized conditions as described herein.

In one particular embodiment, the disclosure provides a method of detecting a nucleic acid chimera formed during the generation of a sequencing library. The method comprises contacting a sample comprising nucleic acids from heterogeneous microbial population with a first tagging polynucleotide and a second tagging polynucleotide. The first tagging polynucleotide comprises a first target annealing sequence at an end domain, a first linker sequence, and a first unique molecular identifier (UMI) sequence domain disposed between the first target annealing sequence and the first linker annealing sequence. The second tagging polynucleotide comprises a second target annealing sequence at an end domain, a second linker sequence, and a second unique molecular identifier (UMI) sequence domain disposed between the second target annealing sequence and the second linker sequence. The first and second target annealing sequences specifically anneal to either side of a taxonomically relevant genomic sequence in the microbial population. The method also comprises amplifying the taxonomically relevant genomic sequence in a first stage to provide, assuming an error-free reaction, a first plurality of amplicons each comprising a first UMI sequence, a taxonomically relevant genomic sequence, and a second UMI sequence. The method further comprises contacting the first plurality of amplicons with a first indexing primer and a second indexing primer. The first indexing primer is a forward primer that comprises a first linker annealing sequence at the 3'-end that anneals to the first linker sequence, a first universal primer annealing sequence, and a first index sequence domain disposed between the first linker sequence and the first universal primer annealing sequence. The second indexing primer is a reverse primer that comprises a second annealing linker sequence at the 3'-end that anneals to the second linker sequence, a second universal primer annealing sequence, and a second index sequence domain disposed between the second linker sequence and the second universal primer annealing sequence. The method comprises further amplifying the taxonomically relevant genomic sequence in a second stage to provide, assuming an error-free reaction, a second plurality of amplicons that comprise the first universal primer annealing sequence, first index sequence, a first UMI sequence, the taxonomically relevant genomic sequence, a second UMI sequence, the second index sequence, and the second universal primer annealing sequence. At least a portion of the plurality of the second amplicons is sequenced with universal primers that anneal to the first and second universal primer annealing sequences. A chimera is detected when the sequences of the first and/or second UMI sequence domain are discordant with other UMI domain pairs for that molecule. In some embodiments, a chimera is detected when the sequence of the first or second UMI sequence domains is not present in a single sequence.

In some further embodiments, the first tagging polynucleotide and second tagging polynucleotide are each part of the same molecular inversion probe that is contacted to the sample, as described in more detail above and in Example 5. In these embodiments, the "first amplification stage" of the embodiments include the extension of the 3'-end and ligation thereof to the 5'-end to provide the single stranded circular molecular inversion molecule. This first amplification stage can comprise further rounds of amplification using the first and second tagging polynucleotides as individual molecular primers, with the later use of indexing primers as the second stage of amplification. Alternatively, after the formation of the single stranded circular molecular inversion molecule, the indexing primers can be employed thereafter as the "second amplification stage."

Other elements of these embodiments can be informed by the descriptions provided above for other aspects of the disclosure.

In another aspect, the present disclosure provides kits for construction of sequencing libraries, as described above. The kits comprise a first tagging polynucleotide molecule, as described herein, that are configured to anneal to a target nucleic acid (e.g., genomic) molecule of interest. The kits can further comprise a second tagging polynucleotide molecule, configured to anneal to target nucleic acid (e.g., genomic) molecule of interest at a side opposite the annealing location as the first tagging polynucleotide molecule. In some embodiments, the first and second tagging polynucleotide can be incorporated into the same single stranded molecule to provide a molecular inversion probe that includes two UMI domains. In further embodiments, the kits further comprise a first indexing primer and second indexing primer, as described herein above. In further embodiments, the kits further comprise additional reverse primers and/or universal primers that can be configured to operate in conjunction with the first and/or second indexing primers to provide for multiple rounds of amplification (e.g., in a two-stage dual indexing procedure), as described above. The kits can provide written indicia to instruct the utilization of the kit components for purposes of generating and potentially sequencing the libraries, as described herein.

It should be understood that the above embodiments, and other embodiments described herein, are provided for explanatory purposes, and are not intended to be limiting.

All publications, patents and patent applications cited herein are hereby expressly incorporated by reference for all purposes to the extent they are consistent with this disclosure.

Methods well-known to those skilled in the art can be used to construct primers and other synthetic nucleic acids, and other analytical tools such as expression vectors and recombinant bacterial cells according to this disclosure. These methods can include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the singular forms "a", "an", and "the" include plural referents unless the context clearly dictates otherwise. For example, reference to a "nucleic acid" means one or more nucleic acids. It is generally noted that the use of the term "or" in the claims is used to mean "and/or" unless explicitly indicated to refer to alternatives only or the alternatives are mutually exclusive, although the disclosure supports a definition that refers to only alternatives and "and/or."

Unless the context clearly requires otherwise, throughout the description and the claims, the words "comprise," "comprising," and the like are to be construed in an inclusive sense as opposed to an exclusive or exhaustive sense, such as in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue. Words such as "about" and "approximately" imply minor variation around the stated value, usually within a standard margin of error, such as within 10% or in some cases 5% of the stated value.

Disclosed are materials, compositions, and components that can be used for, in conjunction with, and in preparation for the disclosed methods and compositions/kits. It is understood that when combinations, subsets, interactions, groups, etc., of these materials are disclosed each of various individual and collective combinations is specifically contemplated, even though specific reference to each and every single combination and permutation of these compounds may not be explicitly disclosed. This concept applies to all aspects of this disclosure including, but not limited to, steps in the described methods and components of the described chamber or system. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

EXAMPLES

The following Examples are illustrative of specific embodiments of the disclosure and various uses thereof. They are set forth for explanatory purposes only, and are not to be taken as limiting.

Example 1

This Example describes exemplary methods and reagents to incorporate a first and an optional second Unique Molecular Identifier (UMI) to an amplicon of a target taxonomically relevant gene to facilitate the sensitive and accurate detection and quantification of operational taxonomic units of microbes in a heterogeneous sample.

Library Preparation

The methods described in this Example are presented in the context of introducing one or two variable length UMIs in the amplicon of 16S rRNA V4 hypervariable region. However, it will be understood that the method and reagents can be repurposed to other target 16S rRNA hypervariable regions (e.g., V1-V3 and V5-V9, combinations thereof, or whole 16S sequencing) or even domains of other taxonomic relevant genetic elements (e.g., 18S rRNA or Internal Transcribed Spacer (ITS) region used for fungal identification).

FIG. 1A schematically illustrates a strategy to add a single UMI and, subsequently, add dual index adaptors for the amplification of the representative hypervariable region V4 of the 16S rRNA gene. First, the genetic material encoding the target 16S V4 region is contacted with a first tagging UMI oligonucleotide primer that contains a sequence that specifically anneals to the target V4 region or to a location near or adjacent thereto at the 5' end (solid "black"). The first oligonucleotide primer also comprises a variable length UMI sequence ("purple") and a customizable sequencer linker sequence ("green"). The customizable sequencer linker sequence provides a specific annealing site for indexing/sequencing primers, applied later. These sequences can vary depending on the sequencing techniques used. The variable length UMI is located between the linker sequence and the sequence that anneals to the target template. The UMI can be a degenerate sequence (or partially degenerate) when in batch form.

As illustrated, a slow anneal phase can be employed to facilitate optimal annealing of the first oligonucleotide primer containing the UMI to the target region prior to the addition of other primers, which include indexes. Illustrative conditions for the slow anneal phase include heating the reaction to about 98° C. for about 2 minutes and cooling slowly at a rate of about 0.1° C. per second to a final temperature of 25° C., as indicated in Table 3. During the annealing phase, the annealed oligonucleotide primers (with UMIs) are extended along the target template. After the slow anneal, dual indexing primers can be added in a one- or two-stage reaction. The two-stage dual indexing reaction is illustrated in FIG. 1A. An embodiment of a one-stage dual indexing approach is illustrated in FIG. 1B, as described in more detail below, which also incorporates a dual UMI strategy. The illustrated one-stage dual indexing strategy that is illustrated can readily be configured into a single UMI strategy, as illustrated in FIG. 1A. An exemplary reaction mixture is set forth in Table 2, which provides the different mixtures for the initial UMI tagging and annealing stage, and the first and second stages of amplification where indexing primers are utilized. In the first stage of amplification, illustrated in FIG. 1A, a first (5' forward) indexing primer and a reverse primer are included for about 26 cycles of amplification. The 5' forward indexing primer anneals to the customizable sequencer linker sequence in added with the first UMI oligonucleotide primer in the primer contacting/slow anneal step (both "green"). The reverse primer includes a sequence that specifically anneals to the target (both in solid "black"), as well as another customizable sequencer linker sequence ("Green"). The customizable linker sequence in the reverse primer is typically different than the linker sequence in the forward indexing primer to provide further annealing sites to a different indexing primer in a later step (see below). Amplification can be performed using cycling conditions indicated in Table 3. The first stage reaction is followed by SPRI cleanup and the method proceeds to the second stage amplification that adds the second indexing primer. In the second stage, a new forward primer, e.g., Illumina P5 primer as shown, is used. The new reverse primer is the second (3' reverse) indexing primer that anneals to the customizable sequencer linker sequence ("green") included in the reverse primer in the prior stage. Further amplification can be performed using cycling parameters indicated in Table 4. The amplicons can be subjected to clean up, as described above, normalization, pooling, and sequencing using platform-specific primers that correspond to the customizable sequencer linker sequence integrated into the primers used in the above library amplification steps (e.g., Illumina primers).

TABLE 2

Reaction mix. The reaction mix is an example for amplification of V4 amplicon of 16S rRNA gene. A first tagging UMI polynucleotide primer (e.g., UMI primer 515F for V4 amplicon) concentration can vary between 100 pM-1 pM, depending on template concentration and desired redundancy. An exemplary reaction at 12.5 pM is detailed. Both stage 1 and stage 2 reaction mix included.

| Component | 1X | 24X | Final concentration |
|---|---|---|---|
| Stage 1 (Initial contact, slow anneal, and stage 1 amplification) | | | |
| 2X KAPA HiFi HotStart Read Mix | 12.5 | 103.00 | 1X |
| SYBR Green (100X) | 0.25 | 6.06 | |
| water | 4.5 | 109.08 | |
| Aliquot by tube | 17.25 | | |
| UMI primer 515F (0.5 nM) | 1.25 | 30.30 | 25 pM |
| DNA (5 ng/uL) | 5 | 121.20 | 25 ng/rxn |
| SLOW ANNEAL | | | |
| 70X-F (10 uM) | 0.75 | 18.18 | 0.3 uM |
| JS083 806R (10 uM) | 0.75 | 18.18 | 0.3 uM |
| Final reaction volume | 25 | | |
| Stage 2 | | | |
| 2X KAPA HiFi HotStart ReadyMix | 12.5 | 300 | 1X |
| 50X-R (10 uM) | 0.75 | | 0.3 uM |
| HS0028 F (P5) (10 uM) | 0.75 | 18 | 0.3 uM |
| water | 10 | | |
| Stage 1 Product (AMPure - 1:100 dilution) | 1 | | |

TABLE 3

Cycling conditions for initial contact, slow anneal, and stage 1 of the dual stage indexing PCR reaction. These are exemplary conditions for single UMI incorporation, followed by the first of a two-stage dual indexing step.

| Temperature (° C.) | Time | Cycles |
|---|---|---|
| 95 | 5 min | 1 |
| 98 | 1 min | 1 |
| 25 | 2 min | 1 - Slow anneal - 0.1° C. per second |
| 98 | 20 sec | 26 cycles |
| 60 | 15 sec | |
| 72 | 15 sec | |
| 4 | forever | 1 |

TABLE 4

Cycling conditions for stage 2 of the dual stage indexing PCR reaction. These are exemplary conditions for the second stage of a two-stage dual indexing step that, in this case, follows a single UMI incorporation step.

| Temperature (° C.) | Time | Cycles |
|---|---|---|
| 95 | 5 min | 1 |
| 98 | 1 min | 1 |

TABLE 4-continued

Cycling conditions for stage 2 of the dual stage indexing PCR reaction. These are exemplary conditions for the second stage of a two-stage dual indexing step that, in this case, follows a single UMI incorporation step.

| Temperature (° C.) | Time | Cycles |
|---|---|---|
| 98 | 20 sec | |
| 60 | 15 sec | 10 cycles |
| 72 | 15 sec | |
| 4 | forever | 1 |

FIG. 1B schematically illustrates a strategy to add two UMI sequences, one at each of the 5' and 3' ends of the taxonomically relevant target gene, and subsequently add dual index adaptors for the amplification of the representative hypervariable region V4 of the 16S rRNA gene. In this specific embodiment, the dual index primers are added in a single step that follows the initial addition of the UMI sequences, as opposed to having a two-stage dual indexing method as illustrated in FIG. 1B. First, the genetic material encoding the exemplary target 16S V4 region is contacted with a first tagging UMI oligonucleotide (forward) primer that contains a sequence (solid "black") that specifically anneals to the target V4 region or to a location near or adjacent thereto at the 5' end and a second tagging UMI oligonucleotide (reverse) primer that contains a sequence (solid "black") that specifically anneals to the target V4 region or to a location near or adjacent thereto at the 3' end. The customizable sequencer linker sequence ("green") in each tagging UMI primer provides a specific annealing site for indexing/sequencing primers added in a subsequence step, which can vary depending on the sequencing techniques used. The variable length UMI domain ("purple") of each tagging UMI primer is located between the linker sequence and the sequence that anneals to the target template. The UMI can be a degenerate sequence, entirely or partially, when in batch form. The amplification can be run at about 20 cycles, after which the indexing primers can be added in a one- or two-stage reaction. The strategy illustrated in FIG. 1B adds the indexing primers in a single stage, with both the forward and reverse indexing primers added simultaneously followed by an additional 10 cycles of amplification. The forward and reverse indexing primers each contain sequences that anneal to the customizable sequencer linker sequences (both in "green") incorporated by the initial UMI primers. Additionally, each of the forward and reverse indexing primers contains indexing sequences ("red") as well as annealing sites ("blue") for forward and reverse sequencing primers (e.g., Illumina P5 and P7 sequencing primers). The resulting amplicons are pooled, normalized, and subjected to sequencing. The PCR reaction mixtures and cycling parameters can be readily adapted from reaction mixtures and parameters set forth in Tables 2-4.

Primer Design

The first tagging UMI (5' forward) primers for 16S amplification were designed according to the general formula:

5'-[Sequencer Linker]-[UMI]-[16S-specific sequence]-3'

The primers can be specifically designed for any V region of 16S (e.g., V1-V9, here for V4) or to any other taxonomically relevant genomic target as are known in the art. Table 5 sets forth non-limiting examples of tagging UMI forward and reverse primers for the 16S V4 and other regions.

TABLE 5

Exemplary UMI primer sequences for 16S variable regions. Designations such as "N1:35151535" at the first N1 position provide the A:C:G:T nucleotide composition in percentages for the degenerate batch at N1 positions in the UMI domain. For example, N1:35151535 indicates 35% A, 15% C, 15% G, and 35% T at the N1 positions in the UMI domain.

| Name | Sequence | SEQ ID NO: |
|---|---|---|
| V4 Forward | | |
| 025, with 14 bp UMI | TCGTCGGCAGCGTCAGATGTGTATAAGAGACAG(N1:35151535)(N1)(N1)(N1)(N1)(N1)(N1)(N1)(N1)(N1)(N1)(N1)(N1)(N1)GTGCCAGCMGCCGCGGTAA | 22 |
| 027, with 12 bp UMI | TCGTCGGCAGCGTCAGATGTGTATAAGAGACAG(N1:35151535)(N1)(N1)(N1)(N1)(N1)(N1)(N1)(N1)(N1)(N1)(N1)GTGCCAGCMGCCGCGGTAA | 23 |
| 082, with 10 bp UMI | TCGTCGGCAGCGTCAGATGTGTATAAGAGACAG(N1:35151535)(N1)(N1)(N1)(N1)(N1)(N1)(N1)(N1)(N1)GTGCCAGCMGCCGCGGTAA | 24 |
| 086, with 10 bp UMI, | TCGTCGGCAGCGTCAGATGTGTATAAGAGACAG(N1:25252525)(N1)(N1)(N1)(N1)(N1)(N1)(N1)(N1)(N1)GTGCCAGCMGCCGCGGTAA | 25 |
| V4 Reverse | | |
| 026, with 14 bp UMI | GTCTCGTGGGCTCGGAGATGTGTATAAGAGACAGG(N1:35151535)(N1)(N1)(N1)(N1)(N1)(N1)(N1)(N1)(N1)(N1)(N1)(N1)(N1)GGACTACHVGGGTWTCTAAT | 26 |
| 028, with 12 bp UMI | GTCTCGTGGGCTCGGAGATGTGTATAAGAGACAGG(N1:35151535)(N1)(N1)(N1)(N1)(N1)(N1)(N1)(N1)(N1)(N1)(N1)GGACTACHVGGGTWTCTAAT | 27 |
| 085, with 10 bp UMI | GTCTCGTGGGCTCGGAGATGTGTATAAGAGACAGG(N1:35151535)(N1)(N1)(N1)(N1)(N1)(N1)(N1)(N1)(N1)GGACTACHVGGGTWTCTAAT | 28 |
| 087, with 10 bp UMI | GTCTCGTGGGCTCGGAGATGTGTATAAGAGACAGG(N1:25252525)(N1)(N1)(N1)(N1)(N1)(N1)(N1)(N1)(N1)GGACTACHVGGGTWTCTAAT | 29 |
| V1-V3 primer designs | | |
| 037 27F, with 14 bp UMI | GTCTCGTGGGCTCGGAGATGTGTATAAGAGACAGG(N1:35151535)(N1)(N1)(N1)(N1)(N1)(N1)(N1)(N1)(N1)(N1)(N1)(N1)(N1)AGAGTTTGATCMTGGCTCAG | 30 |
| 038 534R, with 14 bp UMI | GTCTCGTGGGCTCGGAGATGTGTATAAGAGACAGG(N1:35151535)(N1)(N1)(N1)(N1)(N1)(N1)(N1)(N1)(N1)(N1)(N1)(N1)(N1)ATTACCGCGGCTGCTGG | 31 |

Example 2

This Example describes additional optimized reaction conditions for the single UMI, two-stage dual indexing of the V1-V3 region of 16S rRNA gene.

Extant methods for studying the microbiome associated with skin sites include amplification of the V1-V3 hypervariable region of the 16S rRNA gene. This particular section of the 16S rRNA gene is used because it is able to speciate between different Staphylococcal species, which represent major skin-associated taxa. Described herein are optimized cycling conditions and reaction mixtures that introduce a UMI in the forward primer (27F) prior to amplification and followed by a two-stage dual indexing amplification.

The tagging and amplification approach generally follows the schematic design set forth in FIG. 1, although the figure illustrated different primer sequences. The optimized reaction mixture is set forth in Table 6, which provides the different mixtures for the initial UMI tagging and annealing stage, and the first and second amplification stages where indexing primers are utilized. Contacting, annealing, and first stage of amplification for introduction of a first indexing can be performed using optimized reaction conditions set forth in Table 7. The first stage reaction can be followed by SPRI cleanup and then proceed to the second stage amplification that adds the second indexing primer. In the second stage, a new forward primer, e.g., Illumina P5 primer as indicated in Table 6, is used. The new reverse primer is an indexing primer that anneals to the customizable sequencer linker provided in the reverse primer utilized in the first stage of indexing/amplification. Further amplification is performed using optimized parameters cycling indicated in Table 8. The amplicons are optionally subjected to clean up, as described above, normalization, pooling, and sequencing using platform-specific primers that correspond to the customizable sequencer linker sequence integrated into the primers used in the library amplification steps (e.g., Illumina primers).

TABLE 6

A representative reaction mix per sample for amplification of V-V3 amplicon of 16S rRNA gene. A first tagging UMI polynucleotide primer (UMI primer 27F for V1-V3 amplicon) concentration can be >300 pM, depending on template concentration and desired redundancy. An exemplary reaction at 300 pM is detailed. Both stage 1 and stage 2 reaction mixes are included.

| Component | 1X | 24X | Final concentration |
|---|---|---|---|
| Stage 1 (Initial contact, slow anneal, and stage 1 amplification) | | | |
| 2X KAP A HiFi HotStart ReadyMix | 12.5 | 303.00 | 1X |
| SYBR Green (100X) | 0.25 | 6.06 | |
| water | 4.5 | 109.08 | |
| Aliquot by tube: | 17.25 | | |
| UMI primer 27F (6 nM) | 1.25 | 30.30 | 300 pM |
| DNA | 5 | 121.20 | 25 ng/rxn |
| SLOW ANNEAL | | | |
| 70X-F (1 uM) | 0.75 | 18.18 | 0.03 uM |
| JS083 534R (1 uM) | 0.75 | 18.18 | 0.03 uM |
| Final reaction volume | 25 | | |
| Stage 2 | | | |
| 2X KAPA HiFi HotStart ReadyMix | 12.5 | 300 | 1X |
| 50X-R (10 uM) | 0.75 | | 0.3 uM |
| HS0028 F (P5) (10 uM) | 0.75 | 18 | 0.3 uM |
| water | 10 | | |
| Stage 1 Product (AMPure - 1:100 dilution) | 1 | | |

TABLE 7

Cycling conditions for initial contact, slow anneal, and stage 1 of the dual stage indexing PCR reaction for V1-V3. This approach performs dual indexing using a single step library preparation.

| Temperature (° C.) | Time | Cycles |
|---|---|---|
| 95 | 5 min | 1 |
| 98 | 1 min | 1 |
| 25 | 2 min | 1 - Slow anneal - 0.1° C. per second |
| 98 | 20 sec | |
| 63 | 15 sec | 26 cycles |
| 72 | 15 sec | |
| 4 | forever | 1 |

TABLE 8

Cycling conditions for stage 2 of the optimized dual stage indexing PCR reaction for V1-V3. This approach performs dual indexing using a single step library preparation.

| Temperature (° C.) | Time | Cycles |
|---|---|---|
| 95 | 5 min | 1 |
| 98 | 1 min | 1 |
| 98 | 20 sec | |
| 60 | 15 sec | 10 cycles |
| 72 | 15 sec | |
| 4 | forever | 1 |

Example 3

This Example describes the optimization of UMI adaptors by varying the GC content and concentration of the UMI primers.

Figure 2:
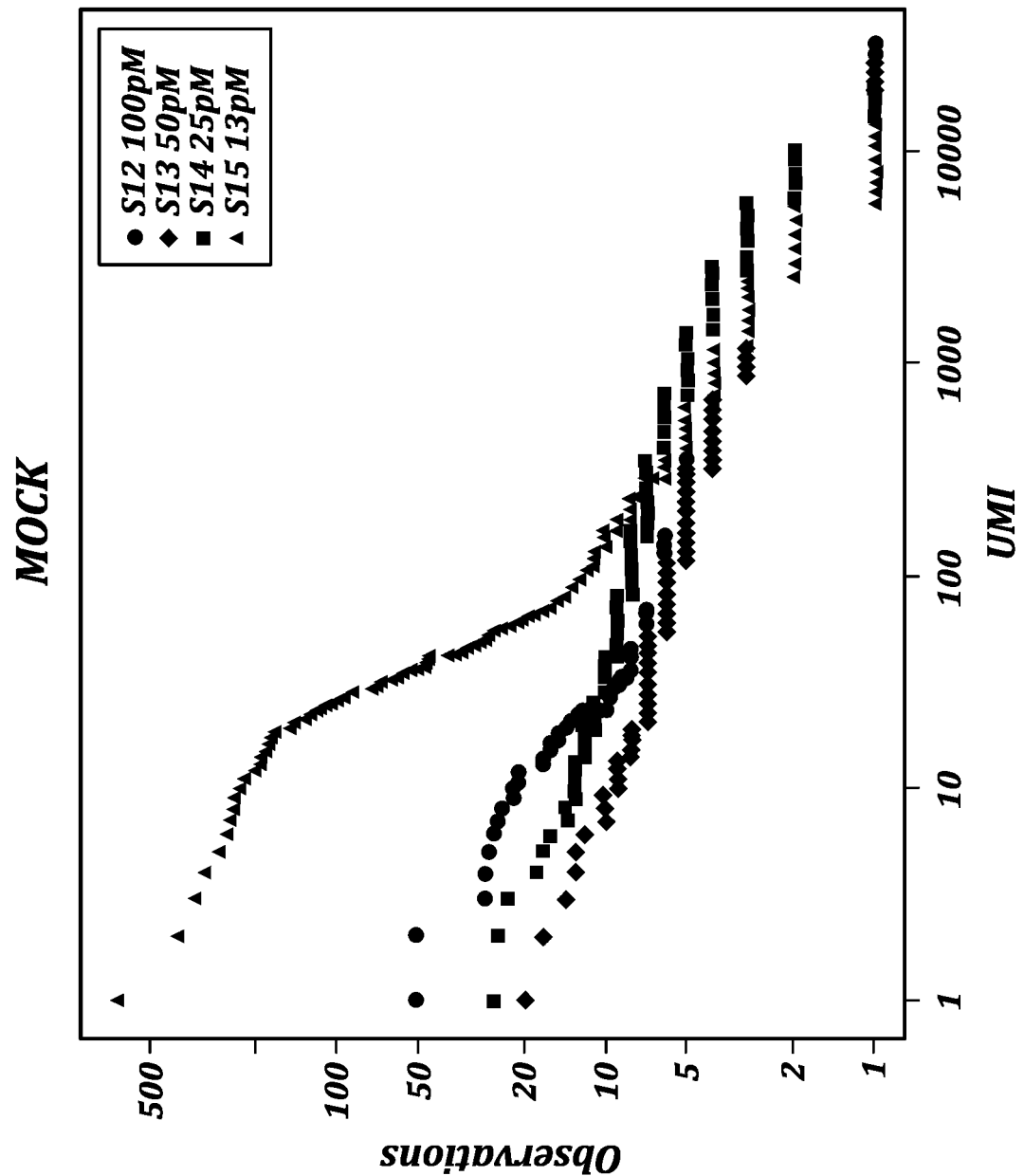
FIG. 2 graphically illustrates the effect variable concentrations of tagging UMI primers on number of observations of each unique UMI using Mock bacterial community (BEI ATCC community HM-783D) DNA as template material for PCR reaction.

The concentration of tagging UMI primers in the described methods can be tuned to increase or decrease the number of observations of each unique UMI at a given read depth. In the single UMI, two-stage dual indexing amplification strategy, described above and illustrated in FIG. 1A, the concentration of the first tagging UMI primer was varied to determine the effect on the number of observations of each unique UMI when generating a sequencing library from a mock heterogenous community sample of microorganisms. BEI ATCC community HM-73D was used as the mock bacterial community DNA sample. Concentrations of 13, 25, 50, and 100 pM of first UMI tagging primer were applied according the strategy illustrated in FIG. 1A and described above and the number of observations of the individual UMI were recorded. FIG. 2 illustrates that decreasing tagging concentration of tagging UMI primers increases the chances of observing any specific unique molecular identifier UMI more than once. Conversely, at higher concentrations of UMI oligonucleotide primers could result in so many UMIs that each would be sequenced only once at limited sequencing depth. It is also observed that lower concentrations of tagging UMI oligonucleotide primers ensure the unique tagging of any particular target molecule because at higher UMI oligonucleotide primer concentrations the same UMI sequence might tag different target molecule, which erodes the efficiency of deduplicating reads.

Figure 3:
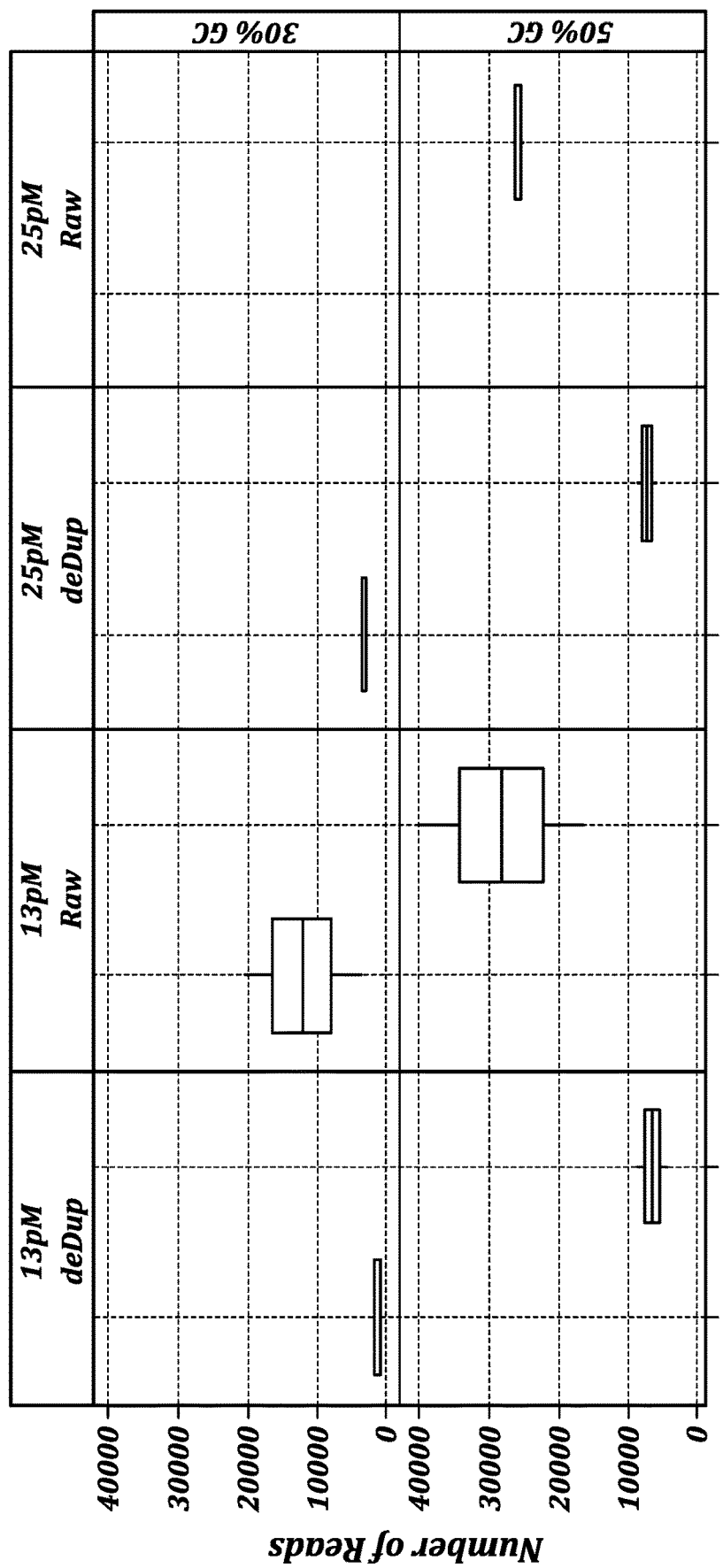
FIG. 3 graphically illustrates the effects of tagging UMI primer concentration and GC content on the number of reads assigned to 97% ID Operational Taxonomical units (OTUs) before ("Raw") and after ("deDup") deduplication. Deduplication is performed after mapping each read to an OTU, with no error correction for UMI identification. Identical UMIs within each sample that share OTU identity are deduplicated.
Figure 4:
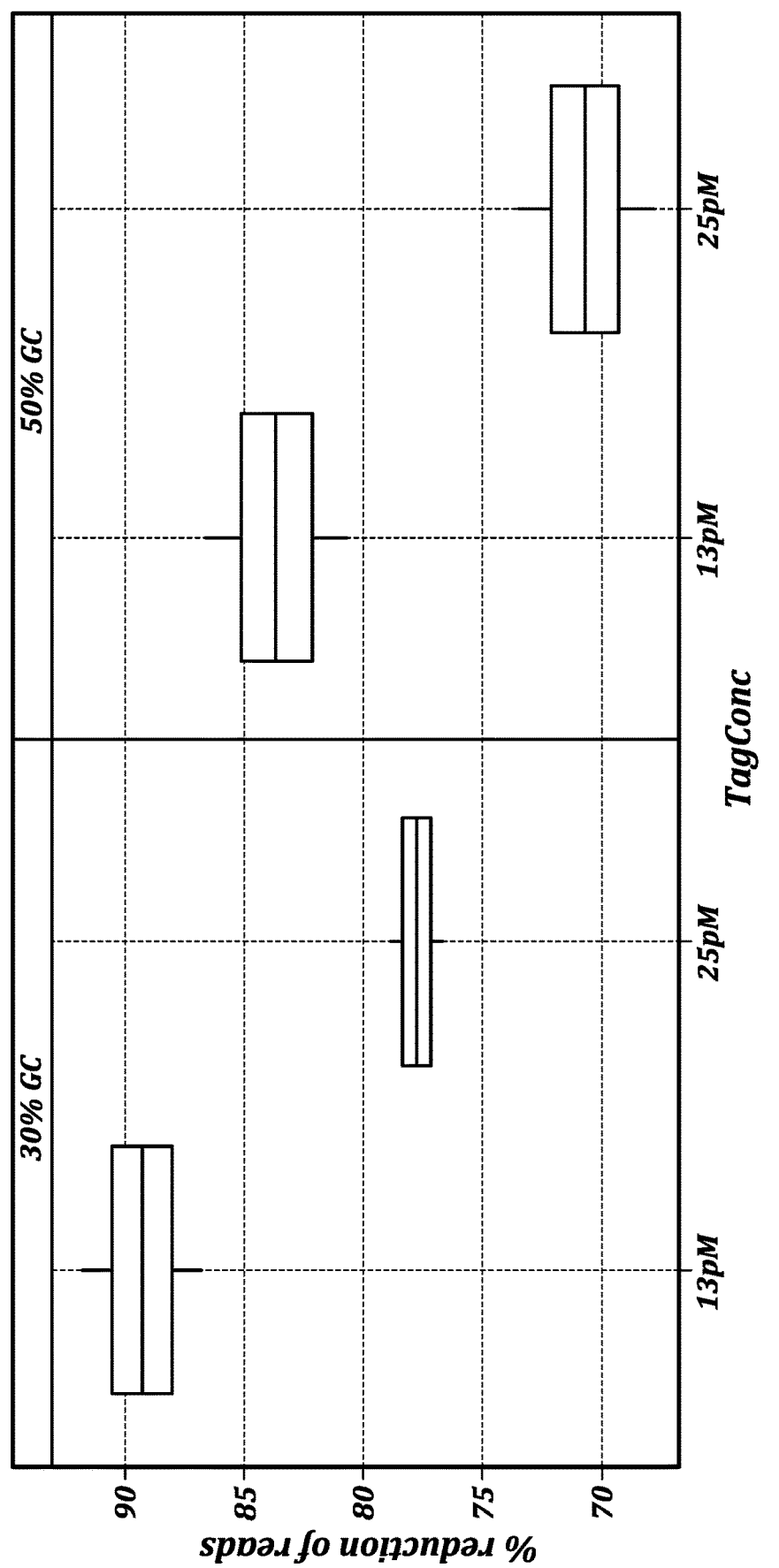
FIG. 4 graphically illustrates the percent reduction in reads assigned to Operational Taxonomical units (OTUs) after ("deDup") deduplication when the reads were obtained using tagging first UMI primers with low (30%) and high (50%) GC content and at low (13 pM) and high (25 pM) concentrations in the reaction.

The influence of the GC content of the tagging UMI primers was assessed on the ability to observe individual UMI in the library. FIG. 3 illustrates the number of reads mapped to different operational taxonomic units (OTUs) from sequenced amplicons generating using first (forward) tagging UMI primers according to the strategy illustrated in FIG. 1A and described in more detail above. The observations are illustrated for first UMI tagging primers with 30% and 50% GC content before and after removal of UMIs after mapping each read to an operational taxonomic unit ("Raw" and "deDup," respectively). These results show that use of low concentration (i.e., 13 pM) of low GC % (30%) tagging UMI primers prior to amplification resulted in the most efficient reading of the OTUs in heterogenous sample given the increased difference between the raw and deDup reads. FIG. 4 graphically illustrates the percent reduction in duplicate reads during deduplication observed for first (forward) tagging UMI primers addressed in FIG. 3. As illustrated, lower (i.e., 13 pM) concentration and lower GC percentage (i.e., 30%) result in the greatest percent reduction in duplicate reads. However, all tested parameters and parameter combinations for primer concentration and GC content show good performance for reducing the number of reads.

These results demonstrate that the disclosed strategy for incorporating a UMI tag target amplicons for taxonomically relevant genetic elements within a heterogenous sample can be optimized by altering the concentration of the tagging UMI primers applied prior to amplification and by altering the GC content of the UMI tags themselves. This approach demonstrates a high efficiency for reducing redundant reads that can overwhelm a metagenomics sequencing analysis and obscure detection of rare sequences.

Example 4

This Example describes further characterizations of the performance of the single UMI, two-stage dual indexing amplification method described in Example 1.

Figure 5:
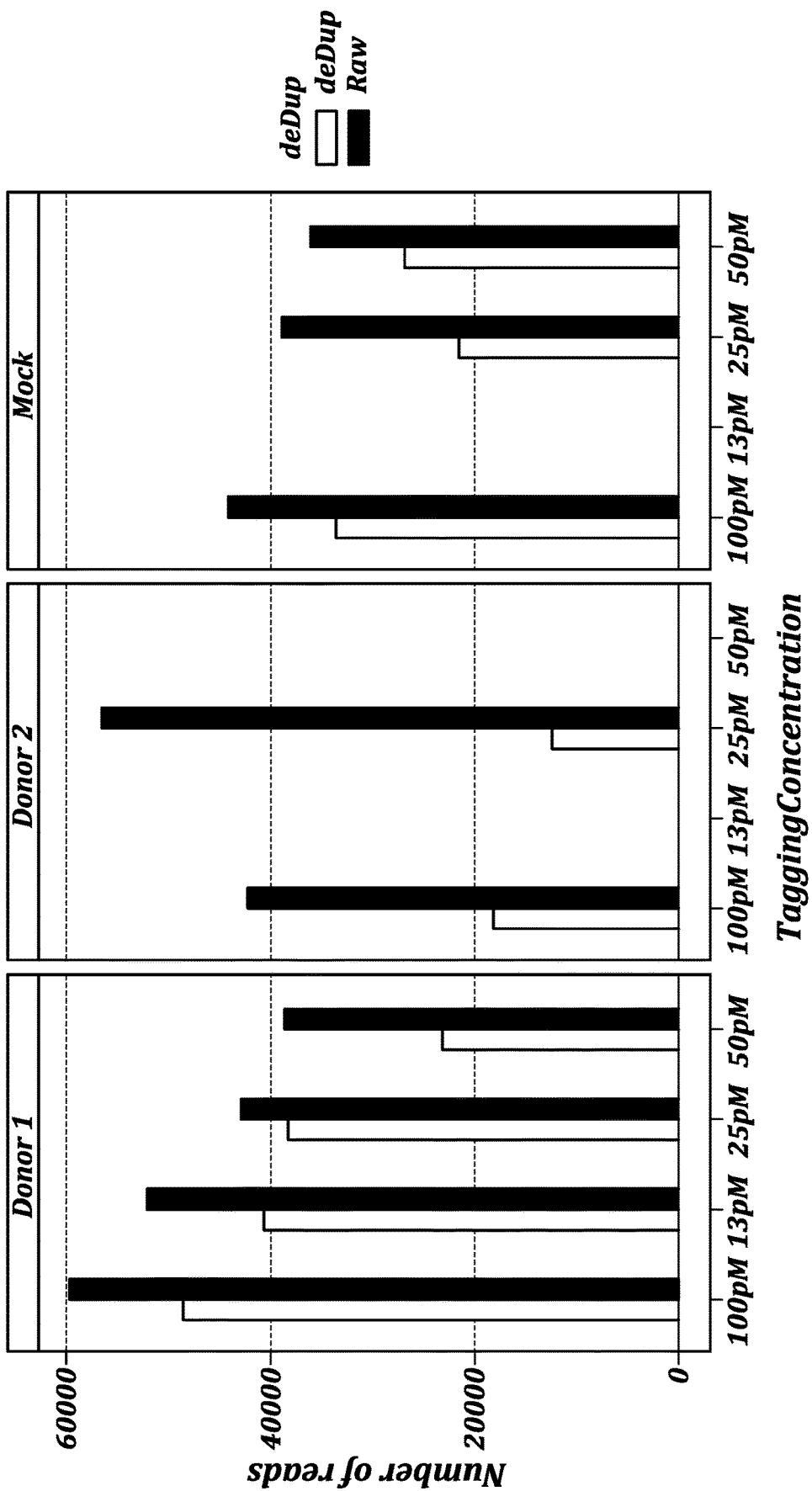
FIG. 5 graphically illustrates reads assigned to 97% ID Operational Taxonomical units (OTUs) before ("Raw") and after ("deDup") deduplication of UMIs. A reduction in assigned reads after deduplication was observed. Deduplication was performed after mapping each read to an OTU. Identical UMIs within each sample that share 97% ID OTU identity were deduplicated. Donor 1 and Donor 2 represent complex fecal communities. The "Mock" group represents community amplified from BEI HM-783D known mock community.
Figure 6:
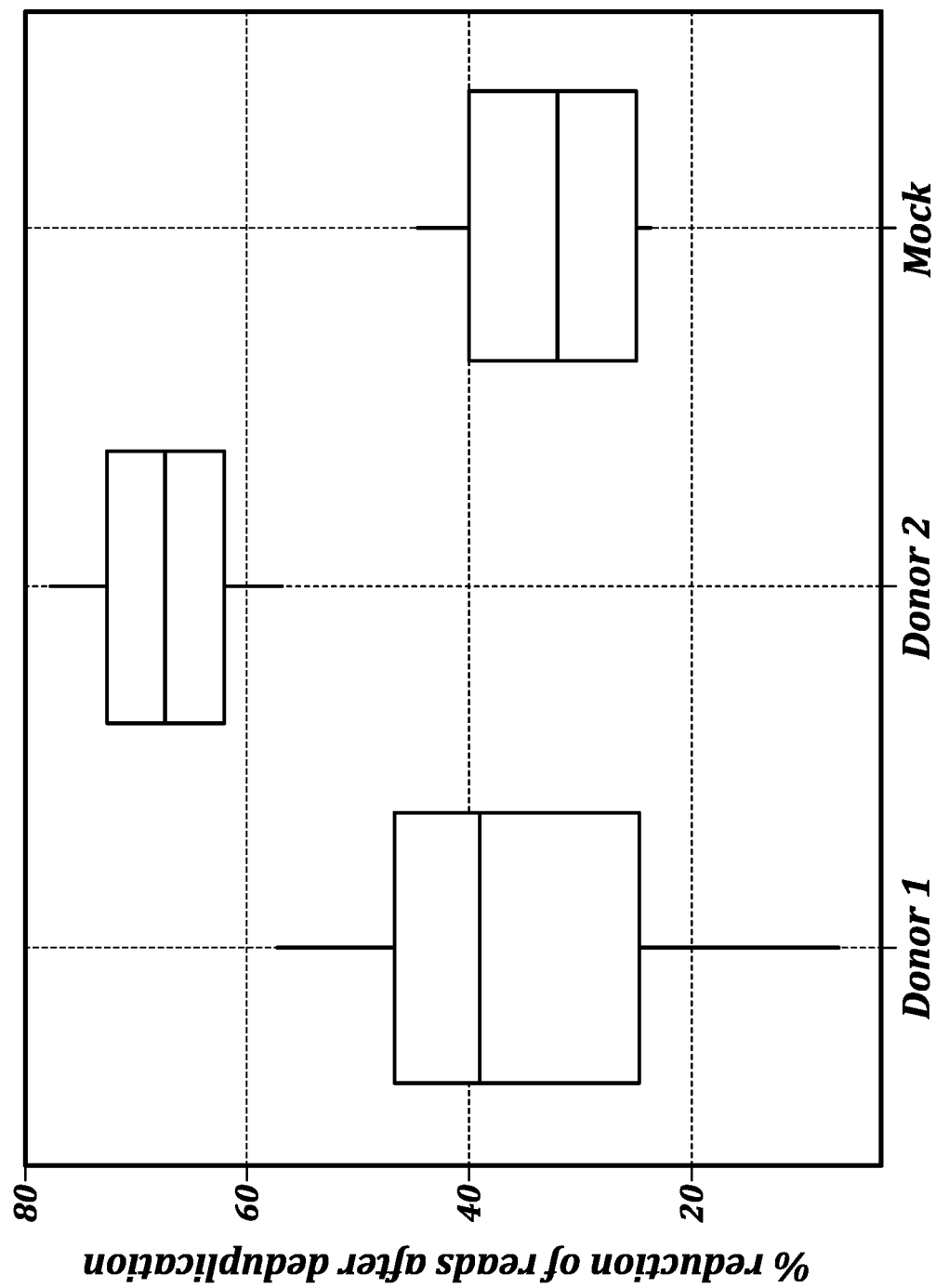
FIG. 6 graphically illustrates the percent reduction of 97% ID OTU-assigned reads after deduplication of UMIs per sample type. Donor 1 and Donor 2 represent complex fecal communities. Mock represents community amplified from BEI HM-783D known mock community.

Complex fecal community samples from two donors, as well as a mock bacterial community (BEI ATCC community HM-783D), were used to generate sequencing libraries using the single UMI, dual two-stage indexing approach described in Example 1 and illustrated in FIG. 1A. The libraries were generated and sequenced in replicates using different concentrations of first UMI tagging primers directed to the V4 region of the 16S rRNA gene. FIG. 5 graphically illustrates reads assigned to OTUs before ("Raw") and after ("deDup") multiple UMIs tagging the same OUT are removed. A reduction in assigned reads after deduplication was generally observed. Deduplication was performed after mapping each read to an OTU. UMIs within each sample that share OTU identity are deduplicated. FIG. 6 illustrates the percent reduction of OTU-assigned reads after deduplication of UMIs per sample type for the libraries characterized in FIG. 5. The illustrated values were determined by calculating the percent deduplicated reads from raw reads for all UMI concentration combinations. This illustrates the percent reduction in duplicated reads that are observed when using the disclosed UMI strategy. When averaged across the donors and mock groups, these data indicate that the described single UMI, dual index approach results in 38±18% reduction of reads assigned to specific operational taxonomical units (OTUs) after singleton correction.

Figure 7:
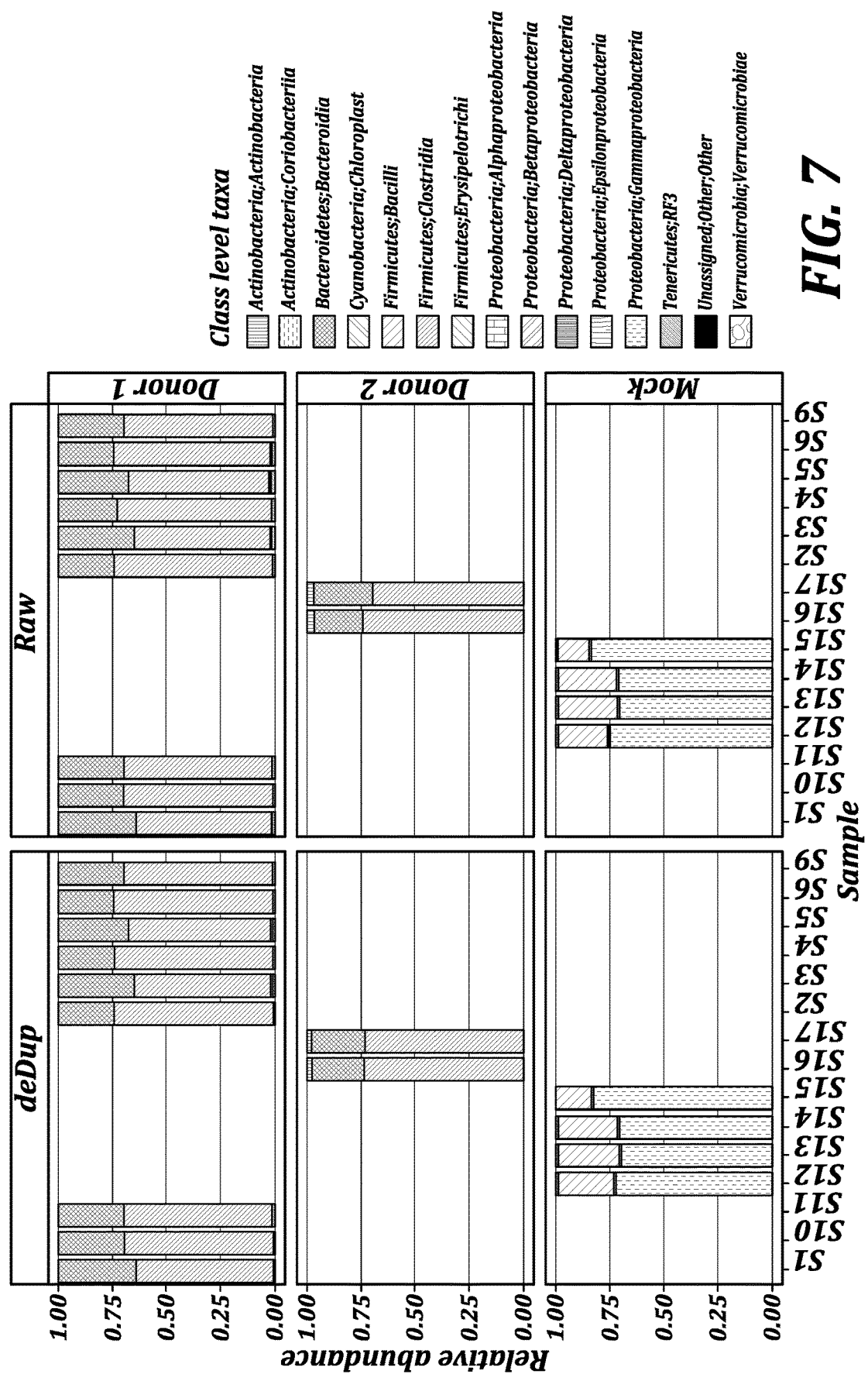
FIG. 7 graphically illustrates the taxonomic distribution before and after deduplicating for multiple sequencing libraries from samples prepared from different microbiotas (S1-S17). Donor 1, Donor 2, and the Mock community (addressed, e.g., in FIG. 5). Relative abundances of class level taxa are shown with no significant changes to taxonomical distribution of class-level taxa after deduplication of unique molecular indexes.

Next, the effect of deduplication correction on the ability of the single UMI, two-stage dual indexing approach to detect the taxonomic distribution was explored. FIG. 7 graphically illustrates the taxonomic distribution before and after deduplication correction from multiple libraries obtained from the Donor 1, Donor 2, and Mock samples (libraries S1-S11 are from Donor 1, libraries S12-S15 are from the Mock sample, and libraries S16 and S17 are Donor 2). Relative abundance of class level taxa is shown before and after deduplication of the raw data (as described above) is shown. No significant changes to taxonomical distribution of taxa after deduplication of unique molecular were observed.

Figure 8:
FIG. 8 graphically illustrates a UniFrac analysis to assess the effect of deduplication strategy on the assessment of population differences. The populations were obtained from samples from three different microbial sources (Donor 1, Donor 2, and the Mock community addressed in FIG. 5). A small effect on weighted UniFrac distances in between samples before (hashed circles) and after (open circles) deduplication was apparent but overall beta diversity showed no significant effect from deduplication.

A UniFrac analysis was performed on the three populations before and after duplication to assess the measured differences between the indicated biological communities observed from Donor 1, Donor 2, and the mock community. FIG. 8 is a graphical display in three dimensions of the multidimentional relationships among the microbial populations. This representation was produced by calculating a distance metric between all pairs of samples, specifically using unweighted UniFrac which is a distance metric that takes into account the taxonomic similarity between samples. Each symbol represents a library. Each axis and the percentage included, indicates the percent variation explained by that dimension (e.g., 80.56% of the variation is explained by the first, "PC1" axis). As illustrated, while there was a slight effect from before (hashed circles) to after deduplication (open circles), there was still not significant effect in beta diversity in between samples.

Figure 9:
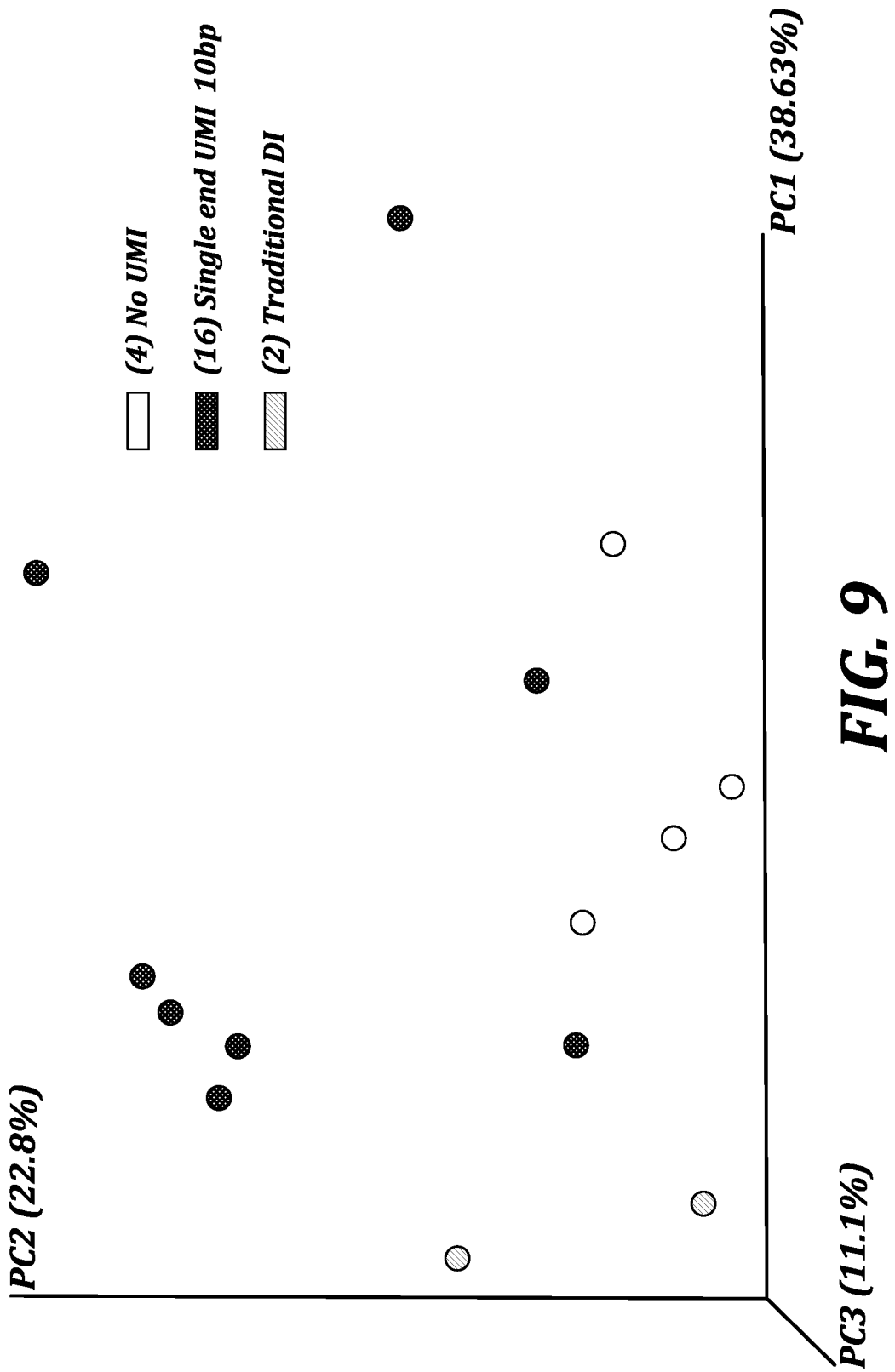
FIG. 9 graphically illustrates a UniFrac analysis of three library preparation strategies of the three microbial populations addressed in, e.g., FIG. 5.

Next, the described single UMI, two-stage dual indexing sequencing strategy, described in Example 1 and illustrated in FIG. 1A was compared against a traditional dual indexing (DI) approach, where no UMIs are included and a single 30 cycle PCR reaction with a 60° C. annealing temperature is used. The traditional DI approach did not include an initial incorporation of UMI prior to amplification in the assessment of the Donor 1, Donor 2, and the mock community microbial populations described above. Additionally, as a control the disclosed single UMI, two-stage dual indexing sequencing strategy was also performed but omitting the first UMI primer. In this approach the same primer design and two stage PCR reactions are used, but no UMI is included in the forward primer. This tests the effect of the UMI inclusion independently of the changes in PCR conditions needed for optimization of the UMI strategy. Unifrac analysis was performed on the raw reads from the library preparations of the three approaches. FIG. 9 graphically illustrates the UniFrac analysis showing the distance between the groups. This Principal Component analysis shows that prior to deduplication the addition of the UMI sequence does not inherently affect the structure of the microbiome.

To test how the deduplication affected taxonomic distribution of the bacteria in the samples studied, libraries from different heterogeneous microbial communities were assessed using the three approaches described above for FIG. 9. Table 9 below sets forth a comparison of OTUs that are differentially represented in the samples from the indicated libraries. The Mean percentages disclosed in the table indicate the relative abundance based on the number of reads observed. These results demonstrate the impact of UMI in determining the correct taxonomical distribution of samples.

TABLE 9

Operational Taxonomic Units (OTUs) that are differentially represented in samples from different libraries of heterogeneous microbial communities. The * indicates the most significant differences between the representation of taxa when determined with and without inclusion if UMIs prior to amplification.

| Library<br>Taxa | Bonferroni_P | Dual Index-single UMI | | Dual Index |
|---|---|---|---|---|
| | | No UMI_mean | sUMI_mean | mean |
| *Actinobacteria; Actinobacteria; Bifidobacteriales Bifidobacteriaceae; Bifidobacterium adolescentis* | 1.15E−14 | 2.39% | 0.08%* | 3.12% |
| *Actinobacteria; Actinobacteria; Bifidobacteriales' Bifidobacteriaceae; Bifidobacterium* spp. | 9.57E−09 | 0.49% | 2.43%* | 0.30%$ |
| *Fimicutes; Clostridia; Clostridiales; Lachnospiraceae; Coprococcus* spp. | 2.76E−04 | 3.21% | 1.87%* | 3.38% |
| *Actinobacteria; Coriobacteriia; Coriobacteriales; Coriobacteriaceae; Eggerthella lenta* | 7.65E−04 | 0.48% | 0.32% | 0.73% |
| *Firmicutes; Clostridia; Clostridiales; Lachnospiraceae; Ruminococcus* spp. | 0.001 | 1.25% | 2.30%* | 0.86% |

TABLE 9-continued

Operational Taxonomic Units (OTUs) that are differentially represented in samples from different libraries of heterogeneous microbial communities. The * indicates the most significant differences between the representation of taxa when determined with and without inclusion if UMIs prior to amplification.

| Library Taxa | Bonferroni_P | Dual Index-single UMI No UMI_mean | sUMI_mean | Dual Index mean |
|---|---|---|---|---|
| Firmicutes; Clostridia; Clostridiales; Ruminococcaceae; Faecalibacterium prausnitzii | 0.003 | 23.10% | 23.60% | 17.70% |
| Bacteroidetes; Bacteroidales; Bacteroidaceae; Bacteroides spp. | 0.025 | 13.20% | 13.20% | 16.70 |
| Firmicutes; Clostridia; Clostridiales; Lachnospiraceae; Roseburia faecis | 0.043 | 4.92% | 5.01% | 3.62% |

This data shows that the initial tagging of target taxonomically relevant genes with UMI prior to amplification and indexing, such as by using the single UMI, dual two-stage indexing approach described in Example 1, can increase the efficiency of library sequencing while preserving the ability to detect the taxa represented in heterogeneous populations.

Example 5

This Example describes performance of a dual UMI tagging approach that utilizes a molecular inversion probe containing both tagging polynucleotides in a single molecule to provide a circularized template for subsequent indexing and amplification steps.

BACKGROUND

As indicated above, incorporating two UMI sequence at either side of taxonomically relevant genomic sequence for sequencing can be advantageous because it increases the complexity of the UMI tagging, as well as allows for the detection of aberrant chimera formation that can occur during library formation and sequencing. However, as described in the Examples above, in certain implementations, a relatively low concentration of tagging polynucleotides (incorporating the UMI domains) is preferable. A major challenge to incorporating two flanking UMIs for taxonomic profiling (and chimera detection) is that both UMI-containing polynucleotides should to be present at limiting dilution. This can impose a severe population bottleneck on the number of molecules that receive two UMIs, because it is typically a low-probability event.

Method

To enhance the incorporation rate of two UMI sequences, i.e., one at either side of the target taxonomically relevant genomic sequence, a molecular inversion probe can be employed that includes two tagging polynucleotides, each with a UMI domain, within a single molecule. FIG. 10 provides a schematic illustration of an embodiment using such a molecular inversion probe that targets the 16S rRNA gene V4 region. At the top of the scheme, the linear inversion molecular probe is shown with the first tagging polynucleotide at the 3'-end and the second first tagging polynucleotide at the 5'-end. The first tagging polynucleotide contains the first linker sequence, the first UMI domain, and the first targeting arm that anneals to or near to the taxonomically relevant genomic sequence and serves as the serves as the primer for extension. The second first tagging polynucleotide sequence contains the second linker sequence, the second UMI domain, and the second targeting arm that anneals to or near to the taxonomically relevant genomic sequence. Both of the first targeting arm and second targeting arm anneal to the target genomic molecule, at locations on either side of the desired taxonomically relevant genomic sequence (here 16S V4). The gap between the first targeting arm and second targeting arm is filled by extension from the first targeting arm, which serves as the primer. Finally, the extended 3'-end reaches the location of the second targeting arm at the 5'-end, whereby the strands are then ligated to produce a circularized, single stranded template. This circularized, single stranded molecular inversion probe template can then be exposed to treatment by an exonuclease to eliminate all single stranded species in solution, thereby reducing background in subsequent amplification, indexing, and sequencing steps, which are performed as described above.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for detecting operational taxonomic units (OTUs) in a heterogeneous microbial population, comprising:
    contacting a sample comprising nucleic acids obtained from the heterogeneous microbial population with a plurality of first tagging polynucleotide primers, wherein the plurality of first tagging polynucleotide primers comprise a unique molecular identifier (UMI) sequence domain disposed between a first linker sequence and a sequence at the 3'-end that specifically anneals to, or anneals near to, a taxonomically relevant genomic sequence in the microbial population, and wherein the UMI sequence domain comprises one or more degenerate sequences;
    providing conditions to allow the plurality of first tagging polynucleotide primers to specifically anneal to a plurality of target nucleic acids in the sample at or near to the taxonomically relevant genomic sequence;
    amplifying the taxonomically relevant genomic sequence to provide a plurality of amplicons comprising at least one of the plurality of first tagging polynucleotide primer sequences and the taxonomically relevant genomic sequence; and
    in at least a portion of the plurality of amplicons, sequencing a segment of the amplicons comprising the first tagging polynucleotide primer sequence and the taxonomically relevant genomic sequence.

2. The method of claim 1, wherein the conditions that allow the plurality of first tagging polynucleotide primers to specifically anneal to the plurality of target nucleic acids comprise cooling the sample from an initial melting temperature at a substantially linear rate of less than 0.5° C. per second for at least one minute.

3. The method of claim 1, wherein the conditions that allow the plurality of first tagging polynucleotide primers to specifically anneal to the plurality of target nucleic acids comprise providing increasing concentration of salt.

4. The method of claim 1, wherein the plurality of first tagging polynucleotide primers comprise at least one locked nucleic acid residue configured to confer increase specificity of the first tagging polynucleotide primers to the locus at or near to the taxonomically relevant genomic sequence.

5. The method of claim 1, wherein each individual UMI sequence of the UMI sequence domain has a GC content of less than about 60%, 55%, 50%, 45%, 40%, 35%, or 30%.

6. The method of claim 5, wherein each individual UMI sequence has a GC content of less than 40%.

7. The method of claim 1, wherein the plurality of first tagging polynucleotide primers are contacted to the sample at a concentration of less than about 100 pM, 75 pM, 50 pM, 25 pM, 2s pM, 15 pM, or 10 pM in the sample.

8. The method of claim 1, further comprising extending at least one of the plurality of first tagging polynucleotide primers along the taxonomically relevant genomic sequence template upon annealing of the at least one first tagging polynucleotide primer to the target nucleic acid.

9. The method of claim 1, wherein amplifying the taxonomically relevant genomic sequence comprises contacting the sample with a first indexing primer and a second indexing primer, wherein the first indexing primer comprises a first indexing domain and a first universal primer annealing domain and the second indexing primer comprises a second indexing domain and a second universal primer annealing domain.

10. The method of claim 9, wherein amplifying the taxonomically relevant genomic sequence comprises two amplification stages,
    wherein the first stage comprises contacting the sample with the first indexing primer that anneals to the first linker sequence and with a reverse primer that comprises a second linker sequence and anneals to a target nucleic acid sequence to provide a first plurality of amplicons, and
    wherein the second stage comprises contacting the first plurality of amplicons with the second indexing primer that anneals to the second linker sequence and a universal primer that anneals to the first universal domain to provide a second plurality of amplicons.

11. The method of claim 10, wherein the first amplification stage comprises between 18 and 30 cycles of the polymerase chain reaction.

12. The method of claim 10, wherein the second amplification stage comprises between 5 and 15 cycles of the polymerase chain reaction.

13. The method of claim 1, further comprising assigning the sequenced amplicons to an OTU based on the determined taxonomically relevant genomic sequence.

14. The method of claim 13, further comprising deduplicating the sequenced amplicons assigned to an OTU, wherein deduplicating comprises collapsing similarly assigned sequenced amplicons with duplicate UMIs into a single representative sequenced amplicon read, or otherwise removing duplicate sequenced amplicons from the assigned OTU that comprise duplicate UMIs.

15. The method of claim 1, wherein the taxonomically relevant genomic sequence comprises a variable region of the 16S rRNA gene, a variable region of the 18S rRNA gene, an Internal Transcribed Spacer region, or a portion thereof.

16. The method of claim 1, wherein the UMI sequence domain comprises one or more constant bases interspersed between multiple degenerate sequences.

17. The method of claim 14, further comprising determining the representation of an OTU in the microbial population by quantitating the deduplicated sequenced amplicons assigned to an OTU.

* * * * *

UNITED STATES PATENT AND TRADEMARK OFFICE
CERTIFICATE OF CORRECTION

| | | |
|---|---|---|
| PATENT NO. | : 10,774,377 B1 | Page 1 of 1 |
| APPLICATION NO. | : 15/726254 | |
| DATED | : September 15, 2020 | |
| INVENTOR(S) | : V. Ridaura et al. | |

It is certified that error appears in the above-identified patent and that said Letters Patent is hereby corrected as shown below:

On the Title Page

Item (72), change "Jerrod George Schwartz" to -- Jerrod Schwartz --

In the Claims

Column 43, Line 53, change "$2_s$" to -- 20 --

Signed and Sealed this
Twenty-first Day of June, 2022

*Katherine Kelly Vidal*

Katherine Kelly Vidal
*Director of the United States Patent and Trademark Office*